(12) United States Patent
Shemesh et al.

(10) Patent No.: US 11,911,137 B2
(45) Date of Patent: Feb. 27, 2024

(54) SENSING AT LEAST ONE BIOLOGICAL PARAMETER, E.G., HEART RATE OR HEART RATE VARIABILITY OF A SUBJECT

(71) Applicant: Cardiacsense Ltd., Caesarea (IL)

(72) Inventors: Eldad Shemesh, Binyamina (IL); Igor Kouperman, Yokneam (IL); Boris Spektor, Haifa (IL)

(73) Assignee: Cardiacsense Ltd., Caesarea (IL)

( * ) Notice: Subject to any disclaimer, the term of this patent is extended or adjusted under 35 U.S.C. 154(b) by 313 days.

(21) Appl. No.: 17/083,561

(22) Filed: Oct. 29, 2020

(65) Prior Publication Data

US 2021/0076957 A1 Mar. 18, 2021

Related U.S. Application Data

(63) Continuation of application No. 15/879,738, filed on Jan. 25, 2018, now Pat. No. 10,849,513, which is a continuation-in-part of application No. 15/079,084, filed on Mar. 24, 2016, now abandoned.

(60) Provisional application No. 62/260,695, filed on Nov. 30, 2015, provisional application No. 62/240,573, filed on Oct. 13, 2015, provisional application No.
(Continued)

(51) Int. Cl.
| | |
|---|---|
| A61B 5/024 | (2006.01) |
| A61B 5/00 | (2006.01) |
| A61B 5/0205 | (2006.01) |
| A61B 5/0245 | (2006.01) |
| A61B 5/117 | (2016.01) |

(Continued)

(52) U.S. Cl.
CPC ...... *A61B 5/02416* (2013.01); *A61B 5/02438* (2013.01); *A61B 5/681* (2013.01); *A61B 5/0205* (2013.01); *A61B 5/02405* (2013.01); *A61B 5/0245* (2013.01); *A61B 5/117* (2013.01); *A61B 5/14532* (2013.01); *A61B 5/349* (2021.01); *A61B 5/4818* (2013.01); *A61B 5/6826* (2013.01); *A61B 5/6844* (2013.01); *A61B 5/6893* (2013.01); *A61B 5/7203* (2013.01)

(58) Field of Classification Search
None
See application file for complete search history.

(56) References Cited

U.S. PATENT DOCUMENTS

| | | |
|---|---|---|
| 2007/0276270 A1 | 11/2007 | Tran |
| 2013/0310700 A1 | 11/2013 | Wiard et al. |

(Continued)

FOREIGN PATENT DOCUMENTS

| | | |
|---|---|---|
| WO | 2018025199 A1 | 2/2018 |

*Primary Examiner* — Jon Eric C Morales
(74) *Attorney, Agent, or Firm* — Dorsey & Whitney LLP

(57) ABSTRACT

The present disclosure concerns a device for sensing at least one biological parameter (e.g., heart rate, heart rate variability) of a subject, the device comprising a contact surface configured for being brought into a contact with a skin surface of the subject. The device has at least one light source for illuminating the skin surface through the contact surface along an illumination source optical axis with illumination including at least one sensing wavelength, and at least one detector for detecting a response of said illumination at least at said wavelength, from the skin surface through the contact surface along a detector optical axis, and providing signals configured for determining said biological parameter based thereon, said illumination optical axis forming with said contact surface an acute included angle.

9 Claims, 21 Drawing Sheets

Related U.S. Application Data

62/194,839, filed on Jul. 21, 2015, provisional application No. 62/194,840, filed on Jul. 21, 2015, provisional application No. 62/169,711, filed on Jun. 2, 2015.

(51) Int. Cl.
    *A61B 5/145*     (2006.01)
    *A61B 5/349*     (2021.01)

(56) References Cited

U.S. PATENT DOCUMENTS

| | | |
|---|---|---|
| 2014/0257049 A1 | 9/2014 | Soundarapandian et al. |
| 2014/0275850 A1 | 9/2014 | Venkatraman et al. |
| 2014/0275852 A1 | 9/2014 | Hong et al. |
| 2015/0230735 A1 | 8/2015 | Venkatraman et al. |
| 2015/0261946 A1 | 9/2015 | Yoon et al. |
| 2016/0029911 A1 | 2/2016 | Lee |
| 2016/0070245 A1 | 3/2016 | Lee et al. |
| 2016/0183818 A1 | 6/2016 | Richards et al. |
| 2016/0317067 A1 | 11/2016 | Lee |
| 2017/0135633 A1 | 5/2017 | Connor |

SENSING AT LEAST ONE BIOLOGICAL PARAMETER, E.G., HEART RATE OR HEART RATE VARIABILITY OF A SUBJECT

RELATED APPLICATIONS

The present application is a continuation application of U.S. patent application Ser. No. 15/879,738 filed Jan. 25, 2018, which is a continuation-in-part of U.S. patent application Ser. No. 15/079,084 filed on Mar. 24, 2016, which claims priority from the following U.S. Provisional Patent Applications: Application No. 62/169,711 filed Jun. 2, 2015; Application No. 62/194,839 filed Jul. 21, 2015; Application No. 62/194,840 filed Jul. 21, 2015; Application No. 62/240,573 filed Oct. 13, 2015; and Application No. 62/260,695 filed Nov. 30, 2015; which are all hereby incorporated by reference in their entirety.

FIELD OF THE INVENTION

The present invention generally relates to the fields of biological sensing devices.

BACKGROUND

Measurement of various biometric parameters has uses ranging from basic healthcare related diagnostics to person/subject authentication for commerce and security. To date, noninvasive measurement of a person's hemodynamic parameters, such as blood pressure, has presented significant technical challenges.

Authentication is an important element in today's massive use of electronic commerce. It is also becoming more and more important for security related applications. One of the biggest problems in electronic commerce is identity theft and/or credit card information theft. In order to mitigate the risk of such theft, collection of additional, unforgeable authentication elements are needed. As of today, the only biometric parameters readily collected for purposes of identification or authentication is fingerprints, which fingerprints are prone to relatively easy cloning or spoofing.

Accordingly, this application addresses the need for collection of biometric parameters, for: (1) authentication (or identification) of a subject; and/or (2) estimation of hemodynamic parameters of a subject.

SUMMARY OF THE INVENTION

The present invention includes methods, circuits, assemblies, devices, systems and associated machine executable code for biological parameter sensing. According to embodiments of the present invention, there may be provided a set of two or more bio-parameter sensors, each sensor of a different sensor type and adapted to sense a different biological parameter of a user. Sensors of different sensor types may be operated in a synchronous manner in order to obtain measurements usable for deriving a biological parameter which is not measurable by any of the operated sensors individually. According to embodiments, each of two or more bio-parameter sensors, of different sensor types, may be operated by control circuitry which is integral or otherwise functionally associated with control circuitry of the other. According to embodiments, two or more of the bio-parameter sensors, of different sensor types, may be part of a common sensor assembly, which sensor assembly may be referred to as a composite sensor assembly. The composite sensor assembly according to embodiments of the present invention my hold two or more of the sensors of different sensor types in a position and orientation relative to each other and relative to a contact surface of the assembly such that both sensors are brought into contact with a contact surface (e.g., skin) of a subject (e.g., person) whose biological parameter is being sensed or derived.

A composite sensor assembly according to some embodiments may include any combination of optical sensors, electrical resistivity sensors, electrocardiogram (ECG) sensors, mechanical pressure sensors, motion sensors (e.g., accelerometers, gyroscopes and magnetometers), temperature sensors Galvanic Skin Response (GSR) sensors and any other sensor usable for measuring a biological parameter. According to embodiments, a first sensor integral or otherwise functionally associated with the composite assembly may be an electrocardiogram (ECG) type sensor which may detect electrical signals generated in connection with and/or during a user's heart beats. According to the same embodiment, a second sensor integral or otherwise functionally associated with the composite assembly may be a photoplethysmogram (PPG) type sensor which may optically sense a user's pulse as blood passes through an arterial of the user which is being optically inspected and/or optically monitored by the PPG. Each respective sensor may include at least one respective sensor element and at least one respective sensing circuit, which sensing circuits may be integral or otherwise functionally associated with one another.

The PPG assembly may include: (1) one or more photo-emitters, (2) one or more photo-detectors, and (3) one or more optical guiding elements (e.g., collimator, lenses, etc.). The PPG may also include circuits to drive the photo-emitter and to process signals generated by the photo-detector. The PPG assembly may include or be functionally associated with a one or more displacement sensors such as motion sensors and/or pressure sensors. Displacement sensors may be positioned with or near the PPG assembly and may be arranged so as to be in physical contact with an area of user's skin at or near the skin area with which the PPG sensors are in contact. Signals generated by the displacement sensors (e.g., pressure sensors), may be used by a PPG related signal processing circuit to compensate for and thus mitigate PPG sensing artifacts, which artifacts may be at least partially due to change of pressure the PPG sensor(s) feels with relation to the skin. This pressure change may be due to movements of fingers tendons and/or palm muscles.

The ECG assembly may include a heartbeat sensor including two or more electrodes, at least one of which electrodes may be connected to an electric signal amplifier. The ECG may include amplification circuit(s) and also circuits to process electrical signals which were generated by the subject's heart, received by the one or more electrodes, and amplified by the amplification circuit(s).

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

In FIG. 8A there is shown a device (e.g., a smartphone) or device case on which two Combined ECG/PPG Units are positioned, and in FIGS. 8C-8D, there are shown, in accordance with some embodiments of the present invention, additional exemplary devices including composite sensor units; and In FIG. 9, there is shown, in accordance with some embodiments of the present invention, an exemplary wearable device incorporating a composite sensor assembly(s) combining ECG type, PPG type, and/or Pressure/Motion type sensors, wherein the device is adapted to provide continuous monitoring of PTT.

FIG. 11A shows the device with a PPG sensor; FIG. 11B shows the device with a PPG and ECG sensors.

FIG. 13A shows a longitudinal cross section of the movement sensor; FIG. 13B shows a longitudinal cross section of the movement sensor worn on a wrist.

Figure 1A:
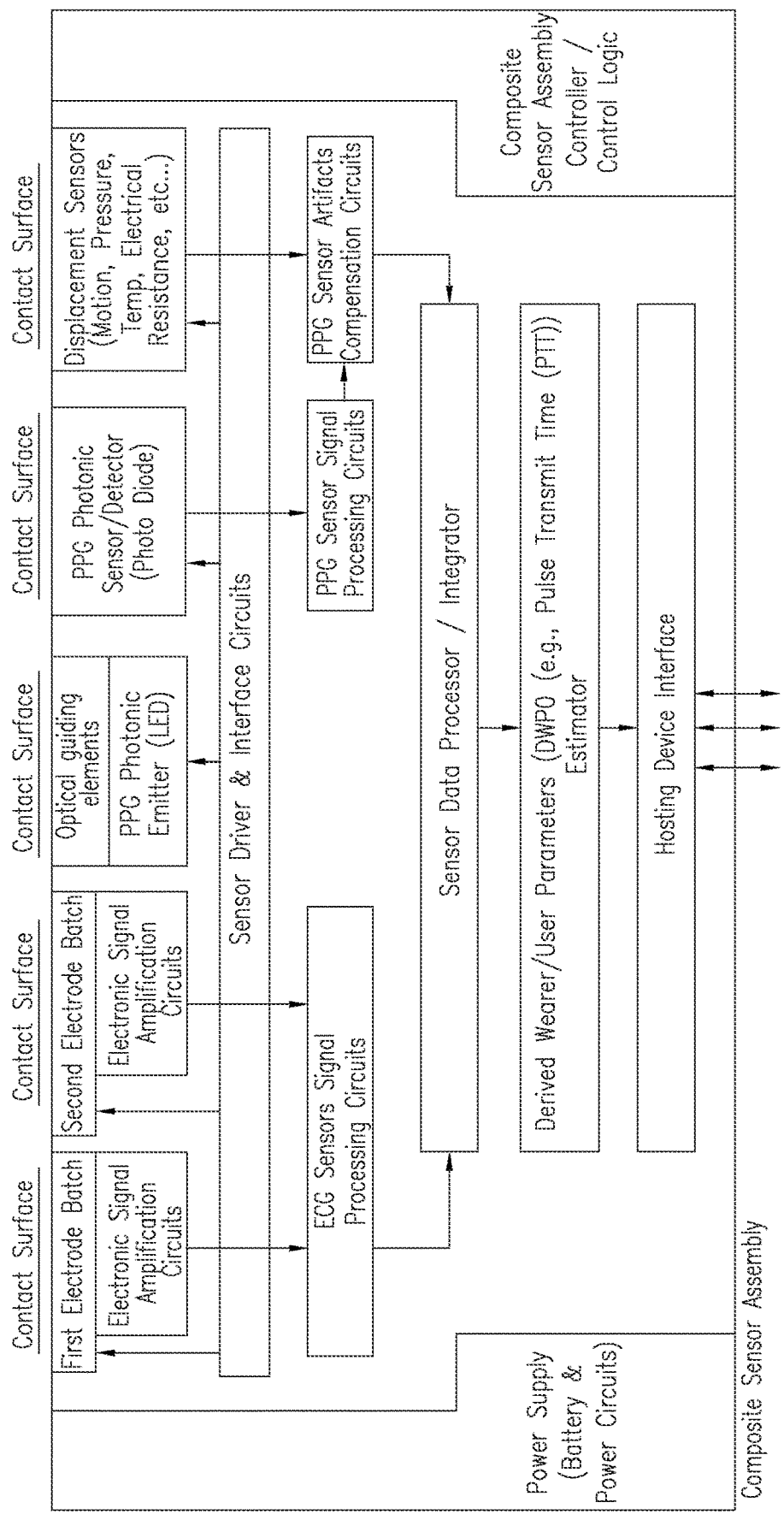
FIG. 1A, is a functional block diagram of an exemplary composite sensor assembly, in accordance with some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Unless specifically stated otherwise, as apparent from the following discussions, it is appreciated that throughout the specification discussions utilizing terms such as "processing", "computing", "calculating", "determining", or the like, may refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In addition, throughout the specification discussions utilizing terms such as "storing", "hosting", "caching", "saving", or the like, may refer to the action and/or processes of 'writing' and 'keeping' digital information on a computer or computing system, or similar electronic computing device, and may be interchangeably used. The term "plurality" may be used throughout the specification to describe two or more components, devices, elements, parameters and the like.

Some embodiments of the invention, for example, may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments of the invention may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a rigid magnetic disk, and an optical disk. Some demonstrative examples of optical disks include compact disk-read only memory (CD-ROM), compact disk-read/write (CD-R/W), and DVD.

In some embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some embodiments, input/output or I/O devices (including but not limited to keyboards, displays, pointing devices, etc.) may be coupled to the system either directly or through intervening I/O controllers. In some embodiments, network adapters may be coupled to the system to enable the data processing system to become coupled to other data processing systems or remote printers or storage devices, for example, through intervening private or public networks. In some embodiments, modems, cable modems and Ethernet cards are demonstrative examples of types of network adapters. Other suitable components may be used.

Functions, operations, components and/or features described herein with reference to one or more embodiments, may be combined with, or may be utilized in combination with, one or more other functions, operations, components and/or features described herein with reference to one or more other embodiments, or vice versa.

General

The present invention includes methods, circuits, assemblies, devices, systems and associated machine executable code for biological sensing. According to embodiments of the present invention, there may be provided a set of two or more bio-parameter sensors, each sensor of a different sensor type and adapted to sense a different biological parameter of a user. Sensors of different sensor types may be operated in a synchronous manner in order to obtain measurements usable for deriving a biological parameter which is not measurable by any of the operated sensors individually.

Composite Sensor Assembly

According to embodiments, each of two or more bio-parameter sensors, of different sensor types, may be operated by control circuitry which is integral or otherwise functionally associated with control circuitry of the other. According to embodiments, two or more of the bio-parameter sensors, of different sensor types, may be part of a common sensor assembly, which sensor assembly may be referred to as a composite sensor assembly. The composite sensor assembly according to embodiments of the present invention may hold two or more of the sensors of different sensor types in a position and orientation relative to each other and relative to a contact surface of the assembly such that both sensors are brought into contact with a contact surface (e.g., skin) of a subject (e.g., person) whose biological parameter is being sensed or derived.

A composite sensor assembly according to some embodiments, may include any combination of optical sensors, electrical resistivity sensors, electrocardiogram (ECG) sensors, mechanical pressure sensors, motion sensors (e.g., accelerometers, gyroscopes and magnetometers), temperature sensors and any other sensor usable for measuring a biological parameter.

According to embodiments, a first sensor integral or otherwise functionally associated with the composite assembly may be an electrocardiogram (ECG) type sensor which may detect electrical signals generated in connection with and/or during a user's heart beats. According to the same embodiment, a second sensor integral or otherwise functionally associated with the composite assembly may be a photoplethysmogram (PPG) type sensor which may optically sense a user's pulse as blood passes through an arterial of the user which is being optically inspected and/or optically monitored by the PPG. Each respective sensor may include at least one respective sensor element and at least one respective sensing circuit, which sensing circuits may be integral or otherwise functionally associated with one another.

PPG Assembly

A PPG assembly may include: (1) one or more photo-emitters, (2) one or more photo-detectors, and (3) one or more optical guiding elements (e.g., collimator, lenses, etc.). The PPG may also include circuits to drive the photo-emitter and to process signals generated by the photo-detector. The PPG assembly may include or be functionally associated with a one or more displacement sensors such as motion sensors and/or pressure sensors.

According to some embodiments, the Photoplethysmography (PPG) type sensor may be used for measuring blood parameters by optical means. Such parameters may include, but are not limited to: heart rate variability, Oxygen saturation, breathing rate, sleep apnea, heart arrhythmias, and/or blood glucose level.

PPG technology may monitor arterial blood volume in the skin. Arterial blood is found, in a substantially large percentage, in the dermis layer. According to some embodiments of the present invention, PPG optics may be built out of at least 2 major elements, wherein the first element may be LED/S that shine the light into the body and the second may be photodiode/s that receive the light of the LED/S reflected back from the body.

According to some embodiments, the design of a PPG sensor, or sensor assembly, may require the setting of some or all the following parameters: number of LEDs, number of photodiodes, height of LEDs in comparison to the photodiodes, distance between LEDs and photodiodes, wavelength used, and/or the LEDs' and/or photodiodes' tilting with regard to the human surface (e.g., skin).

According to some embodiments, the following exemplary designs of a PPG sensor may be implemented, optionally as part of a PPG sensor or sensor assembly, a composite sensor assembly, or a device including such. Tilted LED and/or Photodiode may be used in order for most of the light energy to reach the dermis layer rather than other layers and/or to reflect back to the PD, the LED and or Photodiode (PD) may be tilted such that a minimal energy level is needed by the LED for reaching the dermis layer. Using the same energy level, the amount of light reflected back and sensed by the PD on a tilted LED and PD configuration may be greater than the amount reflected back and sensed by the PD on a non-tilted LED and PD configuration. Accordingly, with the PD and/or the LED tilted, the return from arterial blood will be higher. Further to the above, one or more lenses, and/or one or more additional optical components (e.g., mirrors, collimators), may be added to the LEDs in order of narrowing the beam width and directing more energy into the dermis layer of the skin.

Configuration 1—1 tilted LED and 1 tilted photodiode—tilted LED and photodiode may provide optimal results when a limited number of photodiodes and LEDs is used.

Configuration 2—2 to 4 tilted LEDs—as PD cannot be tilted to 2 or more directions, this configuration includes 1 PD with LEDs positioned on 2 to 4 of its sides. The LEDs may be either tilted, for example towards the PD, or non-tilted. Alternatively, a single, ring shaped, LED around the PD may be used.

Configuration 3—LED within photodiode/s—the PD has a hole, substantially in the middle of it, wherein a LED is positioned. According to some embodiments, in this configuration the LED and photodiode may be combined into a single chip. According to some embodiments, in this configuration there may be provided a buffer between the LED and the PD to prevent direct lighting (not reflected from subject's body) from the LED to the PD. Alternatively, 2 to 4 PDs that surround the LED, and can be served as one combined PD or as 4 separate PDs, may be used.

Configuration 4—Several LEDs embedded within one photodiode—experiments have shown that there may be an optimum point of PD effective area around a LED up to which signal to noise ratio (SNR) increases, and wherein beyond this point SNR starts to decrease. Accordingly, and in order to maximize SNR value, setting the optimal PD area around a LED and duplicating it several times may provide optimal results. According to some embodiments, there may be provided a buffer between each of the LEDs and their respective surrounding PDs, to prevent direct lighting from the LED to the PD. Alternatively, 2 to 4 PDs that surround the LED, and can be served as one combined PD or as 4 separate PDs, may be used.

According to some embodiments, optical pressure sensor(s) may be added to part or all of the described LED-PD configurations.

PPG Displacement Sensors

According to some embodiments, displacement sensors, that may include, but are not limited to, any combination of motion sensors and/or pressure sensors, may be positioned with or near the PPG assembly and may be arranged so as to be in physical contact with an area of user's skin at or near the skin area with which the PPG sensors are in contact. Signals generated by the displacement sensors (e.g., pressure sensors), may be used by a PPG related signal processing circuit, and/or may process outputs of the PPG related signal processing circuit, to compensate for and thus mitigate PPG sensing artifacts, which artifacts may be at least partially due to movement of the PPG sensor(s) resulting from pulse pressure induced movement of the skin with which the PPG sensor(s) are in contact. As PPG displacement sensors feel tendons movements and wrist muscles movement, this type, or similar types, of sensor/s may be used as gesture control sensors.

According to some embodiments of the present invention, an exemplary PPG sensor integrated with a Pressure Sensor may include an upper section made of a Flexible Membrane Surrounding a Non-Compressible Material, for making contact with a body part of a subject (e.g., the finger of a wearer of a composite sensor watch/band); and a lower section made of a Compressible Optically Transmissive Material for absorbing pressure induced by contact made by the body part of the subject (e.g., finger skin) and providing respective pressure indicative signals. The Optically Transmissive Material of the lower section may allow for the functionality of the PPG sensing elements, namely the passage of light from an Emitter to reach the body part of the subject (e.g., finger skin), and to at least partially reflect back to a Photo Diode generating respective PPG signals. Pressure indicative signals may be used to compensate for and thus mitigate PPG sensing artifacts, which artifacts may be at least partially due to change of pressure the PPG sensor(s) feels with relation to the skin.

ECG Assembly

The ECG assembly may include a heartbeat sensor including: (1) two or more electrodes, wherein at least one of which electrodes may be connected to (2) an electric signal amplifier. The ECG assembly may include amplification circuit(s) and also circuits to process electrical signals which were generated by the subject's heart, received by the one or more electrodes, and amplified by the amplification circuit(s).

Combined ECG Type Sensor and PPG Type Sensor Outputs

According to some embodiments, combining ECG type sensor and PPG type sensor outputs may enable the measurement of a subject's Pulse Transmit Time (PTT)—the time it takes the blood wave to travel from the heart to the measurement area (e.g., wrist) of a subject (e.g., a person). According to some embodiments, combining ECG type sensor and PPG type sensor outputs may further enable the measurement of a subject's: Heart Rate, Heart Rate Variability, Breathing Rate, Blood Pressure, and, Heart Arrhythmias (such as Atrial Fibrillation and Cardiac Arrest).

According to some embodiments, the measurement/estimation/detection of some or all of these additional subject bio-parameters/conditions may be enabled/facilitated by the use of one or more corresponding pressure sensors for providing subject associated pressure signals to enable the calculation/estimation and/or adjustment/tuning of the calculated/estimated ECG and/or PPG based bio-parameters of the subject. According to some embodiments, a second PPG sensor in/on the outer part of a wearable band/watch device, may trigger its operation based on pressure sensor(s) signals indicating pressure change/increase (e.g., resulting from finger of wearer contact).

Devices Including Composite Sensor Assembly

According to some embodiments of the present invention, there may be provided a mobile electronic device including two or more bio-parameter sensors, and/or a composite sensor assembly as described hereinbefore. The device may, for example, take the form of a wearable device such as, but not limited to, a wristband or wristwatch.

According to some embodiments, control circuitry of the device may be adapted to activate and regulate operation of each one of the two or more bio-parameter sensors, wherein regulating may include coordinating or synchronizing operation of the sensors relative to one another. The control circuitry may be further adapted to coordinate operation of the two or more sensors so as to collect bio-parameter data sufficient for generating Derived Wearer Parameters (DWP), wherein a DWP may be defined as a biological and/or physiological parameter of the wearer which is not directly measureable by any one of the two or more sensors.

A device according to embodiments of the present invention may include ECG sensors, PPG sensors, skin electrical resistance/impedance/conductance sensors (e.g., GSR sensors), motion sensors, pressure sensors etc. The device may further include control circuitry such as a dedicated control circuit or a programmable processor running an application designed to control the device. According to embodiments, the device may include user interface circuits to interact with a wearer/user and/or communication circuits to communicate with external devices. According to some embodiments, measurement/monitoring of output signals from the ECG, GSR and/or PPG sensors may enable the control circuit to determine, for some or any given moment in time, whether and/or which of the sensors are: attached to, being worn by, and/or currently in contact with the skin of, the user or not.

According to some embodiments, A wearable device may comprise: an inner PPG assembly, in substantially constant contact with the wearer's body/skin, for measurement of heart associated parameters (e.g., HRV, Heart Arrhythmias); and an outer PPG assembly, which by default is not in contact with the wearer's body/skin, for SPO2 (Pulse Oximetry) purposes. The outer PPG assembly, upon the wearer/user making contact with it by placing a finger, from an opposite hand to the hand on which the device is worn, on it; may: provide SPO2 (Pulse Oximetry) parameters of the wearer, which parameters may only be measured, or substantially accurately measured, from a subject's finger; and act as a second ECG electrode node/lead, in addition to a first ECG electrode node/lead of the inner PPG assembly.

A wearable device according to embodiments of the present may, for example, be in the form of a wristwatch, a wristband, a heap-band and/or any other wearable article suitable to be positioned and/or fastened onto the limb or torso portion of a wearer. Biometric data collected by a device according to embodiments of the present invention may be used for a variety of purposes including, but not limited to: diagnostics, therapeutics, wearer authentication and/or human machine interfacing.

The wearable device according to embodiments of the present invention may further include wired and/or wireless communication circuits to transmit to an external computing device/system/platform data from one or more of the device sensors, and/or DWP data.

According to further embodiments, the device's communication circuits may further be adapted to receive data or commands from an external computing device/system/platform. The wearable device may receive instructions and/or commands as to: (1) which bio-parameters to sense, (2) when to sense bio-parameters, (3) at which intervals to sense the bio-parameters, (4) sensor configuration settings, and/or (5) how to process and convey sensed and/or processed data.

A wearable device according to embodiments of the present invention may further include encryption circuits. The encryption circuits may be used to encrypt data transmitted by the device and/or to decrypt data or commands received by the device.

According to some embodiments, the encryption circuits may form a client node of an authentication network, which network optionally further includes an authentication server node. According to such embodiments, the authentication server node may indirectly compare reference data to which the server has access against data collected and/or generated by the device (e.g., bio-parameter data, DWP etc.), using a challenge and answer methodology/scheme which allows for verification of a match between the reference data and the device data, possibly without either the device or the server actually transmitting their respective data.

The data comparison methodology/scheme according to embodiments of the present invention may be substantially similar to schemes used to validate data stored on a SIM card, according to the present invention's methodology/scheme, however, the data to be compared to the reference data may be dynamically acquired by the wearable device.

A wearable device according to embodiments may receive instructions or commands through its communication circuits and/or via its encryption circuits.

According to some embodiments, a composite sensor assembly combining ECG type and PPG type sensors may, for example, be implemented as an assembly for installation on, and/or as an integral part of, the following devices, instruments, machines, and/or wearables. In the following examples, a first (or inner) combined ECG/PPG unit may comprise at least a first PPG sensor and a first electrode(s)/electrode-batch/electrode-node of an ECG sensor, and a second (or outer) combined ECG/PPG unit may comprise at least a second electrode(s)/electrode-batch/electrode-node of the ECG sensor and possibly a second PPG sensor (e.g., for deriving SPO2 (Pulse Oximetry) parameters of the wearer).

According to some embodiments of the present invention, the Combined ECG/PPG Unit may include: a PPG Sensor Assembly comprising LED(s) to emit light and Photo Diode(s) (PDs) to generate signals based on light emitted by the LEDs and reflected from the skin of a subject. The PPG Sensor Assembly may be integrated-into/positioned-within a Pressure Sensor(s) used for mitigating PPG sensing artifacts. The Pressure Sensor(s) and its hosted PPG Sensor Assembly may be collectively positioned within/substantially-at-the-center-of/adjacent-of' an ECG Sensor Assembly Pad. Accordingly a subject/user/wearer of the device may make contact with all three sensors—ECG, PPG, and Pressure—as part of a single 'contact generating' touch of the Combined Unit.

Examples of devices incorporating a composite sensor assembly(s) combining ECG type, PPG type, and/or Pressure/Motion type sensors may include, but is not limited to, the following type of devices:

(1) A wristwatch, pulse oximeter, smartwatch, smartband—where one combined ECG/PPG unit is placed in the inner side of the watch/band and one in the outside;
(2) A Phone/Smartphone—with two combined ECG/PPG units on the back of it;
(3) A case for smartphone or mobile device—with two combined ECG/PPG units in it;
(4) A laptop—with two combined ECG/PPG units on both sides of it;
(5) A bicycle/motorcycle—with two combined ECG/PPG units on both sides of the handlebar;
(6) A wheelchair—with two combined ECG/PPG units on both sides of the handlebars;
(7) A treadmill—with two combined ECG/PPG units on both sides of the handlebars;
(8) A steering wheel of a car—with two or more combined ECG/PPG units on it;
(9) An elliptical exercising machine—with two combined ECG/PPG units on both handles;
(10) An earbud, earphones, hearing aid—with two combined ECG/PPG units on the back or frame of it and/or within the in-ear pieces; and/or
(11) Glasses—with two combined ECG/PPG units on the back of it, and/or one in each of the nose-pads/nose-pad-arms/temples/temple-tips.

According to some embodiments, an exemplary wristband/watch device may comprise a PPG assembly having a PPG sensor on the inner part of the band/watch for monitoring heart rate on a continuous base. The wristband device may further comprise an ECG assembly having one or more leads/electrodes, wherein at least one lead/electrode is on the inner part of the band/watch and at least one lead/electrode is on the outer part of the band/watch. According to some embodiments, when analysis of the PPG sensor outputs indicates heart irregularities, the wrist band/watch may notify the band/watch wearing user. Upon the notified user placing a finger, from the hand opposite to the hand on which the band/watch is worn, making contact with at least one of lead(s)/electrode(s) on the outer part of the band/watch, the ECG RR (e.g., inter-beat) interval may be measured. If analysis of the ECG outputs indicate substantially similar user arrhythmia as indicted by the PPG analysis, the wrist band/watch may notify the band/watch wearing user and/or a networked device/system (e.g., of: an emergency center, a personal assistant, a medical crew member, a life support system).

According to some embodiments of the present invention, a device incorporating a composite sensor assembly(s) combining ECG type, PPG type, and/or Pressure/Motion type sensors, may be adapted to provide continuous monitoring of PTT. According to some embodiments, a composite sensor assembly(s) incorporated device for continuous PTT monitoring, for example a wristband/watch device, may comprise: (1) A Connection Port on the body of the device (e.g., side of device) for accepting a connection jack; (2) Two or more ECG Pads for connecting to two sides of a subject's body (e.g., two sides of the subject's chest) while collectively and continuously monitoring ECG signals from the subject's heart; and (3) A Connection Cable for connecting between, and carrying ECG signals between, the two or more ECG Pads on the subject's side and the connection jack on the device side, wherein the Connection Cable may take the form of a single cable splitting into two or more smaller cables or wires on its ECG pads side, or the form of a main cable including multiple cables/wires.

According to some embodiments, the processing circuits of the composite sensor assembly or composite sensor device—based on the continuously monitored ECG signals provided through the connection jack and port, when combined with continuously monitored PPG signals provided by the PPG sensor and/or pressure/motion sensor(s) of the composite sensor device/assembly as described herein—may generate continuous PTT readings, and thus continuous blood pressure readings of the device using/wearing subject.

Diagnostic Embodiments

According to some embodiments of the present invention, a device, and/or a composite sensor assembly, may measure or derive, directly or indirectly, bio-parameters such as heart rate, electrocardiogram (ECG) waveforms, photoplethysmogram (PPG) waveforms, Pulse Transmit Time (PTT), Augmentation Index, Age Index, Perfusion Index and blood pressure (BP).

According to some embodiments, a first sensor integral or otherwise functionally associated with a composite sensor assembly, and/or a device including a composite sensor assembly (e.g., a wearable device), may be an electrocardiogram (ECG) type sensor assembly which may detect electrical signals generated in connection with and/or during a wearer's heart beats. A second sensor integral or otherwise functionally associated with the composite sensor assembly, and/or with the device including a composite sensor assembly (e.g., wearable device), may be a photoplethysmogram (PPG) type sensor assembly which may optically sense a wearer's pulse as blood passes through an arterial of the wearer which is being optically inspected and/or optically monitored by the PPG. Each respective assembly may include at least one respective sensor element and at least one respective sensing circuit.

According to some embodiments, an exemplary wearable device including a composite sensor assembly with an ECG sensor may include a first batch of one or more electrodes on an inner surface of a watchband or wristband used to affix the wearable device to a limb of the wearer. The wearable device may include a second batch of one or more electrodes on the outer surface of the band, which second batch of one or more electrodes may be positioned such that it may be touched by a device wearer's limb (e.g., hand) opposite to the limb on which the device is affixed or otherwise placed. Accordingly, the first batch of electrodes may receive electrical (ECG) signals through the arm on which the device is placed while the second batch of electrodes may receive electrical (ECG) signals through the arm opposite to the one on which the device is worn.

According to some embodiments, the ECG sensor may be configured to activate and to sample ECG signals when the wearer touches the second ECG electrode. According to further embodiments, the device could be activated when the outer surface electrodes come in contact with a chest of the wearer.

According to some embodiments, the watch or wristband may include 2 ECG wires to connect to ECG pads that are placed over the chest of the device user/wearer and monitor various heart arrhythmias scenarios, including Cardiac Arrest.

The wearable device according to embodiments may include some combination of sensors selected from the group including: (1) ECG sensors, (2) PPG sensors, (3) GSR sensors, (4) temperature sensors, (5) pressure sensors, and/or (6) motion sensors (e.g., accelerometers, gyroscopes, magnetometers). The wearable device may also include one or more device control circuits, for example one or more dedicated controllers and/or one or more programmable general purpose microprocessors. The one or more control circuits may be adapted to activate the sensors, coordinate operation of the sensors, and to receive output signals from both the ECG sensors, the PPG sensors and/or any additional sensors included the wearable device.

Activation of a device according to embodiment of the present invention may be responsive to: (1) a user input through one or more user input elements, such as the ECG electrode or an external pressure sensor; (2) an external instruction or command received through the device's communication circuits; (3) a clock or timer triggered signal; and/or (4) a specific hand gesture control.

Control circuits according to embodiments of the present invention may be adapted to process and output signals or data received from some or all of the two or more sensor assemblies on the wearable device. The output may be to a native display of the wearable device (such as smartwatch or smart glasses display) and/or to an external computing device via the communication circuits of the wearable device.

The wearable device according to embodiments may also include or be otherwise functionally associated with signal processing circuits adapted to estimate or derive one or more biological parameters of the wearer based upon either one or both of the sensor output signals (e.g., ECG and PPG sensors), and/or optionally in combination with output signals of one or more additional sensors (e.g., pressure sensor, temperature sensor).

For example, a composite sensor assembly, and/or a device including a composite sensor assembly according to embodiments of the present invention may be adapted to estimate a wearer's blood pressure based on the ECG and PPG outputs. By comparing an ECG sensor output signal against a PPG sensor output signal, corresponding to the same heartbeat, the control circuit and/or associated signal processing circuits may estimate a pulse transmit time (PTT) value which can then be used to estimate biological or hemodynamic parameters of the wearer, for example the wearer's blood pressure.

More specifically, a delay between detection of a given heartbeat of a subject by an electric signal detector (e.g., electrocardiogram—ECG) and detection of the same given heartbeat by an optical sensor (e.g., PPG) monitoring arterial vessels on a limb of the subject (e.g., wrist) may be measured. The time delay between these two detections may be referred to as a Pulse Transmit Time (PTT) and may be used to estimate: (1) the subject's blood pressure, and (2) the subject's blood vessels elasticity.

The composite sensor assembly's, and/or the device's, processing circuitry may estimate a subject's blood pressure by estimating his Pulse Transmit Time (PTT) and from it calculating the subject's Pulse Transmit Velocity (PTV). Generally, the stiffer a wearer's arteries, the faster blood flows through the arteries. Accordingly, calculations based on assumptions that the PTV is substantially linearly related to blood pressure are usable as part of formulas which estimate blood pressure based on PTV.

In the following exemplary articles, incorporated hereto by reference in their entirety, there are numerous descriptions of various estimation formulas for estimating/deriving blood pressure, and/or other bio-parameters or bio-conditions, of a subject, based on measured PTT and/or PTV values:

Ye, Soo-young, et al. "Estimation of systolic and diastolic pressure using the pulse transit time." Soft Computing 188 (2010): 12761; and Marcinkevics, Zbignevs, et al. "Relationship between arterial pressure and pulse wave velocity using photoplethysmography during the post-exercise recovery period." Acta Univesitatis Latviensis: Biology 753 (2009): 59-68.

Authentication Embodiments

According to some embodiments of the present invention, output signals of one or more of the two or more, composite sensor assembly and/or device, sensors may be used to provide wearer authentication. Bio-parameter sensors of the composite sensor assembly, and/or of the device, may sense and convey one or more of a wearer's bio-parameters for comparison against pre-stored reference bio-parameters (such as angle of PPG systolic slope, absence of dicrotic notch, level of augmentation index, age index, PTT etc.), which reference bio-parameters may be associated with an identity the wearer has declared. A comparison match between the sensed bio-parameters and the reference bio-parameters may result in an authentication that the wearer is in fact whom they declare themselves to be.

According to some embodiments of the composite sensor assembly, and/or the device, output signals from the ECG and/or from the PPG may be sampled, characterized and/or otherwise used for wearer authentication purposes. The ECG may sample one or more heartbeat related electrical signals while the PPG may sample one or more heartbeat related hemodynamic patters (e.g., pulse pattern).

A wearer authentication module integral or otherwise functionally associated with the assembly/device may receive, characterize and/or compare signals received from the ECG and/or the PPG against one or more references. The one or more references may be in the form of one or more values, one or more signal patterns and/or one or more signal pattern characterizations. The one or more references may be stored on the assembly/device and/or on storage integral or otherwise functionally associated with an authentication server (e.g., transaction authentication server, login authentication server, service access authentication server, home security authentication server, etc.). The authentication module and/or authentication server may be accessed by the assembly/device via the assembly's/device's communication circuits and optionally through an external computing device with which the composite sensor assembly, and/or the device, is in contact during an authentication process or flow.

Examples of reference bio-parameters may include repeating ECG signal waveform segments, or characterizations thereof. The waveforms may be detected and sampled from a given person, stored and used for comparison based authentication of the given person at a later time. Likewise, repeating PPG waveforms segments, or characterizations thereof, may be detected, sampled, stored and used for comparison based authentication of the person at a later time. According to some embodiments, a person's motion time, for example the movement of their right arm, palm and/or fingers as they make a gesture with their hand, may be detected (e.g., by use of: pressure sensors, accelerometer and/or gyroscopes based sensors), sampled and stored for comparison based authentication at a later time.

According to some embodiments, comparison based authentication may include calculating a statistical similarity between sets of numbers representing the sensed bio-parameters and the reference bio parameters. According to some embodiments, comparison based authentication may include calculating a statistical similarity between sets of numbers representing the sensed motion characteristics and the reference motion characteristics. According to some embodiments, comparison based authentication may include some combination of sensed bio-parameter data sets and motion characteristic data sets against respectively corresponding reference data sets.

According to some embodiments, bio-parameters which may be used to authenticate a person may include, but are not limited to: PPG characteristics such as systolic time, diastolic time, a ratio of the systolic and diastolic times, a slope of a diastolic period, dicrotic notch availability, DC level (Direct Current level—i.e. part of the signal that has substantially minor changes through time), and/or the like; and/or ECG characteristics such as angles between each element of the ECG cycle. Capacitive sensor readings may also be used.

Authentication of a user/wearer may be performed via a composite sensor assembly, and/or device, according to the present invention when the user/wearer attempts to access a computing device and/or to engage in a commercial transaction. For example, as part of an authentication process of a purchaser.

According to embodiments of the present invention, a wearer of a device according to embodiments may use the device to authenticate themselves for purposes of engaging in a transaction such as a cashless or credit based purchase (e.g., credit card purchase, debit card purchase, vendor provided credit purchase), a cash withdrawal and/or a funds transfer.

According to such embodiments, a wearer's biological and/or biometric parameters may be sensed by the device, and/or a composite sensor assembly functionally associated or integrated with the device, at or about the time of the transaction, and compared against reference parameters stored in a database or data repository. The assembly/device may also sense motion parameters of the wearer, alone or in conjunction with sensing the bio-parameters, while the wearer is gesturing a specific gesture, and may convey the motion parameters for comparison to records stored in a database for comparison. One or more stored reference parameters may be associated with an individual whose identity has been verified or who is otherwise known. The parameters sensed by the assembly/device, at or near the time of a transaction, may be compared to reference parameters associated with a declared identity, namely the identity declared by the wearer as they attempt to engage in the transaction. If the assembly/device sensed parameters sufficiently match (e.g., with sufficient statistical certainty) reference parameters stored in the repository and associated with the identity declared by the wearer as part of the transaction, and assuming the declared identity is authorized to engage in such transaction, the wearer may be authenticated for purposes of the transaction.

According to embodiments, the composite sensor assembly, and/or the wearable device, may communicate, via its wired or wireless communication circuits, with a Point of Sale (PoS) device or other computing device/system/platform through which a transaction may be effectuated, collectively to be referred to as a PoS.

Upon the composite sensor assembly, and/or the wearable device, according to embodiments senses one or more biological parameters and/or one or more motion parameters of the wear, the wearable device may transmit the one or more sensed parameters, or derivatives thereof, to the PoS. The PoS may receive the one or more biological parameters along with an identification of the device wearer's declared identity. The PoS may access a functionally associated database or repository having stored reference biological parameters and/or stored motion parameters, as described above, for known individuals in order to compare the parameters received from the device with stored reference parameters for the declared identity. The PoS may function in accordance with the authentication flow described above.

FIGURE DESCRIPTIONS

In FIG. 1A, there is shown a functional block diagram of an exemplary composite sensor assembly, in accordance with some embodiments of the present invention. The assembly shown in FIG. 1A includes an ECG sensor assembly including a first and a second electrode batch/lead and their respective signal amplification circuits. Also shown is a PPG assembly, including a photonic emitter with optical guiding elements and a photonic detector/receiver; and displacement sensors. The sensors are connected to a sensor driver and interface circuits, and the ECG and PPG sensors are connected to respective signal processing circuits. PPG sensor processed signals are relayed to compensation circuits for adjusting PPG sensor artifacts based on signals from the displacement sensors. Processed ECG signals and adjusted PPG signals are integrated by a mutual sensor data processor and relayed to a derived wearer/user parameter estimator for calculating bio-parameter estimations based on data from at least two of the sensors. Estimated parameters are then relayed to a hosting device interface for presentation and/or further communication to a functionally associated and/or networked device/system/platform. Also shown in FIG. 1A are power supply circuits, such as a rechargeable battery, and a composite sensor assembly controller.

Figure 1B:
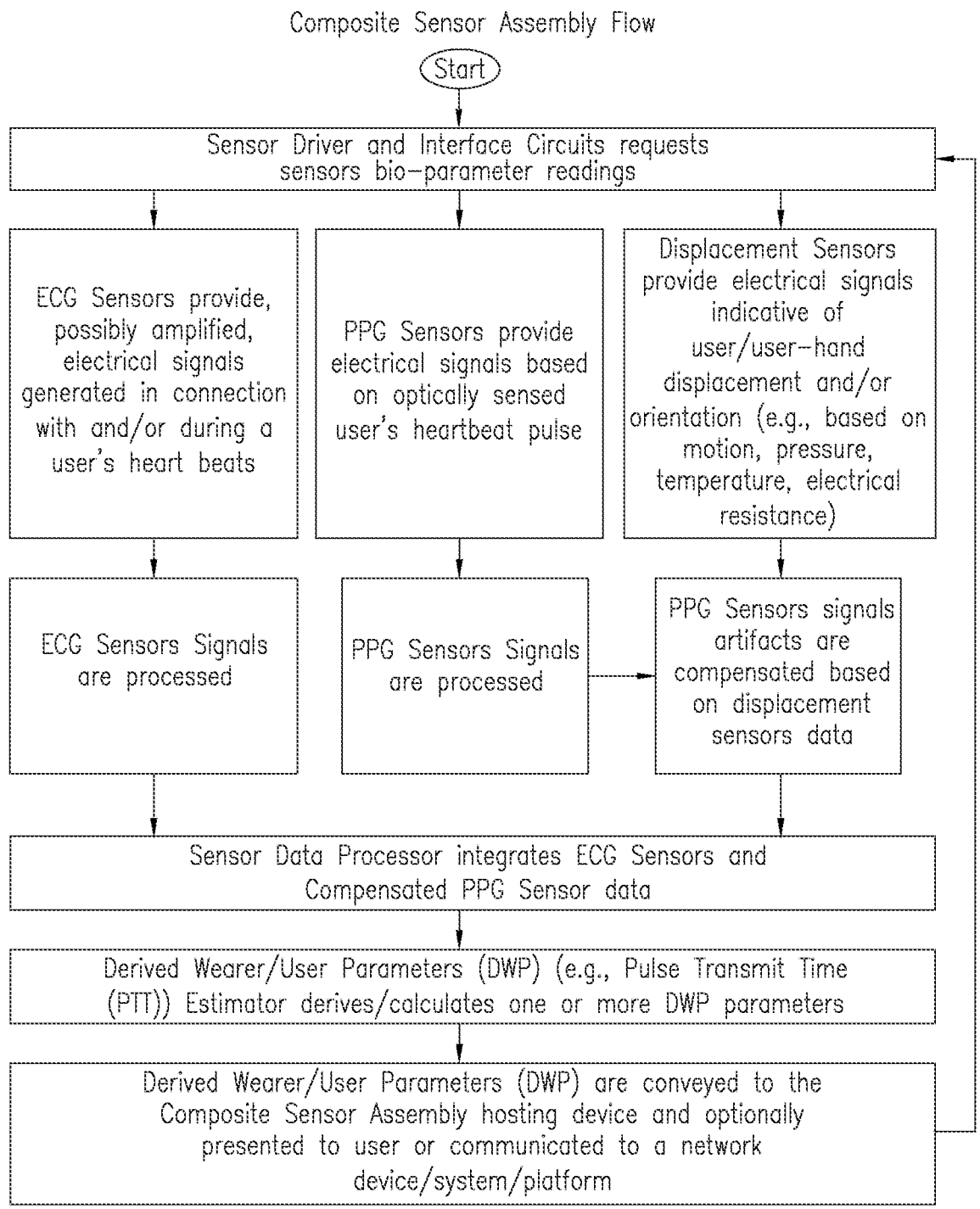
FIG. 1B, is a flowchart of the process and main steps executed by an exemplary composite sensor assembly, in accordance with some embodiments of the present invention.

In FIG. 1B, there is shown a flowchart of the process and main steps executed by an exemplary composite sensor assembly, in accordance with some embodiments of the present invention.

Figure 2A:
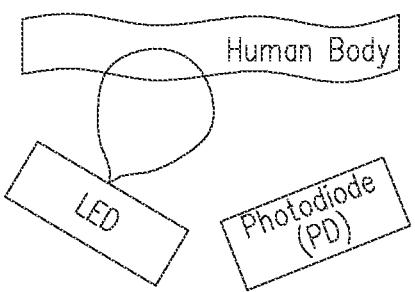
FIGS. 2A-2D, show exemplary design configurations of LED(s) and Photodiode(s) of a PPG sensor, in accordance with some embodiments of the present invention.
Figure 2B:
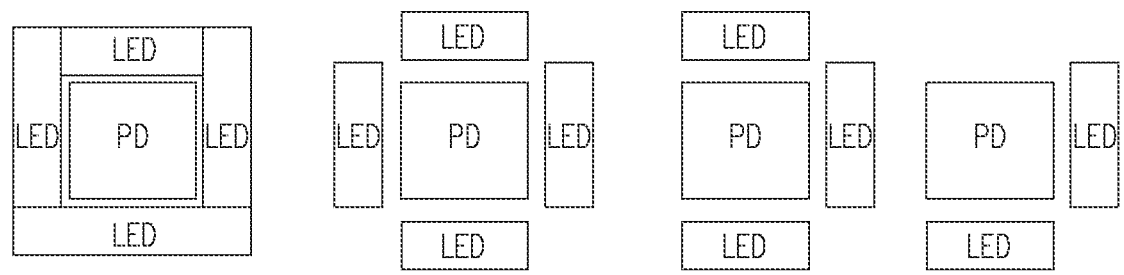
Figure 2C:
Figure 2D:
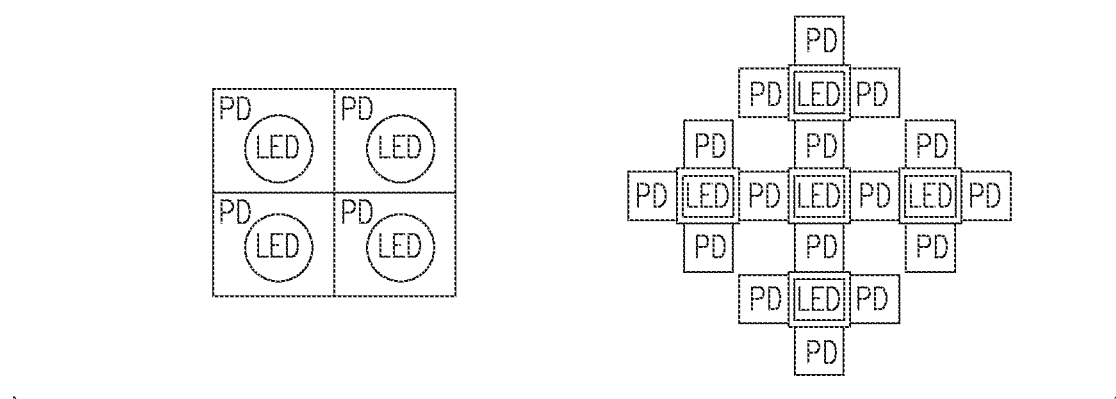

In FIGS. 2A-2D, there are shown exemplary design configurations of LED(s) and Photodiode(s) of a PPG sensor, in accordance with some embodiments of the present invention. The configurations show include: configuration 1—1 tilted LED and 1 tilted photodiode (FIG. 2A); configuration 2—2 to 4 tilted LEDs (FIG. 2B); configuration 3—LED within photodiode/s (FIG. 2C); configuration 4—Several LEDs embedded within one photodiode (FIG. 2D).

Figure 3A:
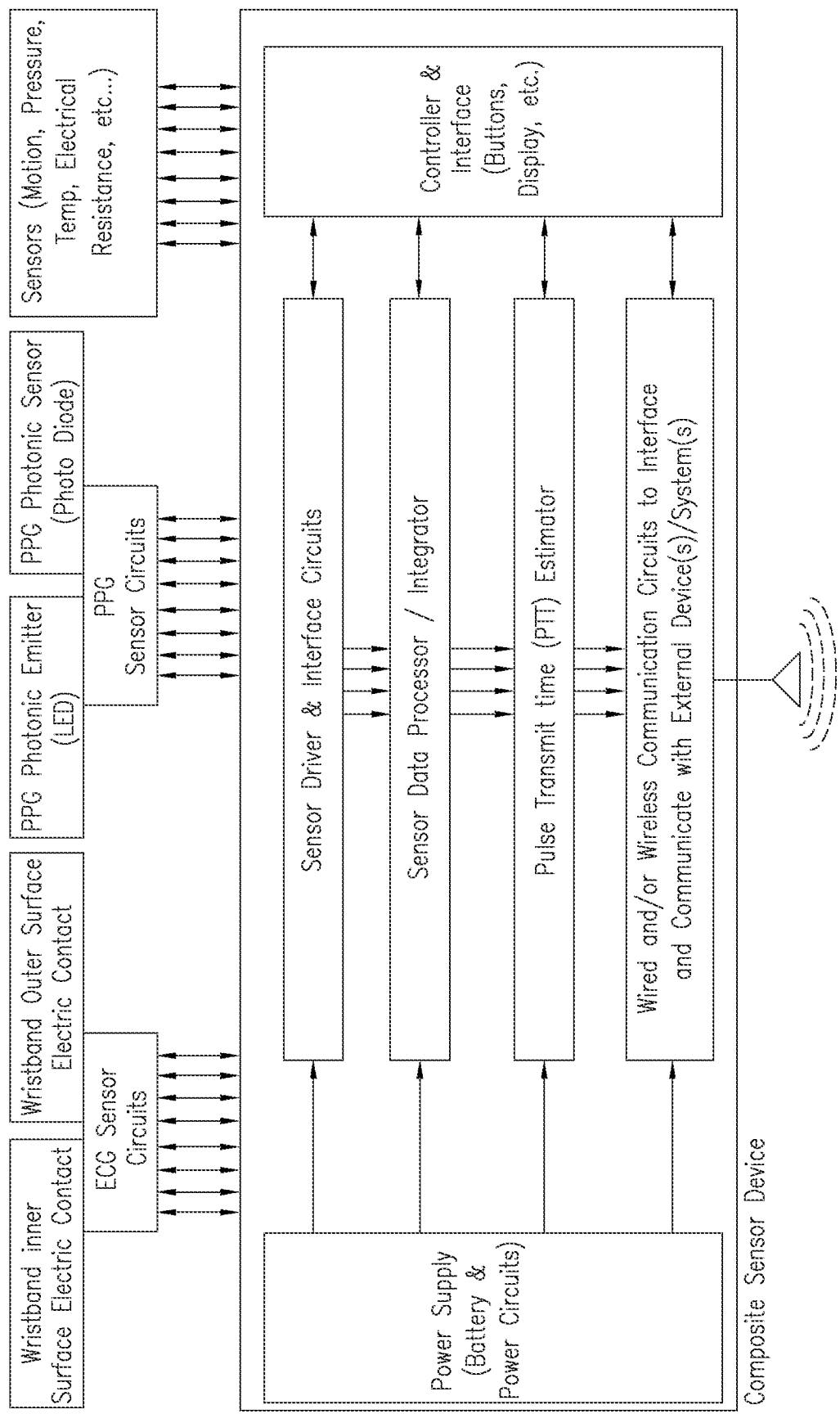
FIG. 3A, is a functional block diagram of an exemplary wearable device, in accordance with some embodiments of the present invention.

In FIG. 3A, there is shown a functional block diagram of an exemplary wearable device, in accordance with some embodiments of the present invention. The device shown in FIG. 3A includes an ECG sensor assembly including ECG circuits connected to a first and to a second contact/electrode-batch/lead. Also shown is a PPG assembly including PPG circuits connected to a photonic emitter and to a photonic receiver. Additional sensors connected to the device include: (1) Motion Sensors, (2) Pressure Sensors, (3) Temperature Sensors, (4) Electrical Resistance/Impendence Sensors, etc. The device according to FIG. 3 also includes a power supply, such as a rechargeable battery, a controller, a display and wearer/user input interfaces. Sensor driver and interface circuits may receive signals or data from each of the respective sensors, and data processor(s) including a PPT estimator that may convert various combinations of raw sensor data into biometric parameter estimations. The data processor(s) may also convert raw motion and/or pressure sensor signals or data into motion indicators usable for tracking movements and/or gestures made by a user, for example as part of an authentication process.

The device shown in FIG. 3A also includes wired and/or wireless communication circuits configured to interface with external devices and/or systems such as: (1) point of sales systems, (2) authentication servers, (3) health tracking systems, etc. The communication circuits may be bidirectional and may receive instructions and/or parameters from an external device, which instructions and/or parameters may configure or otherwise impart operation of the device.

Figure 3B:
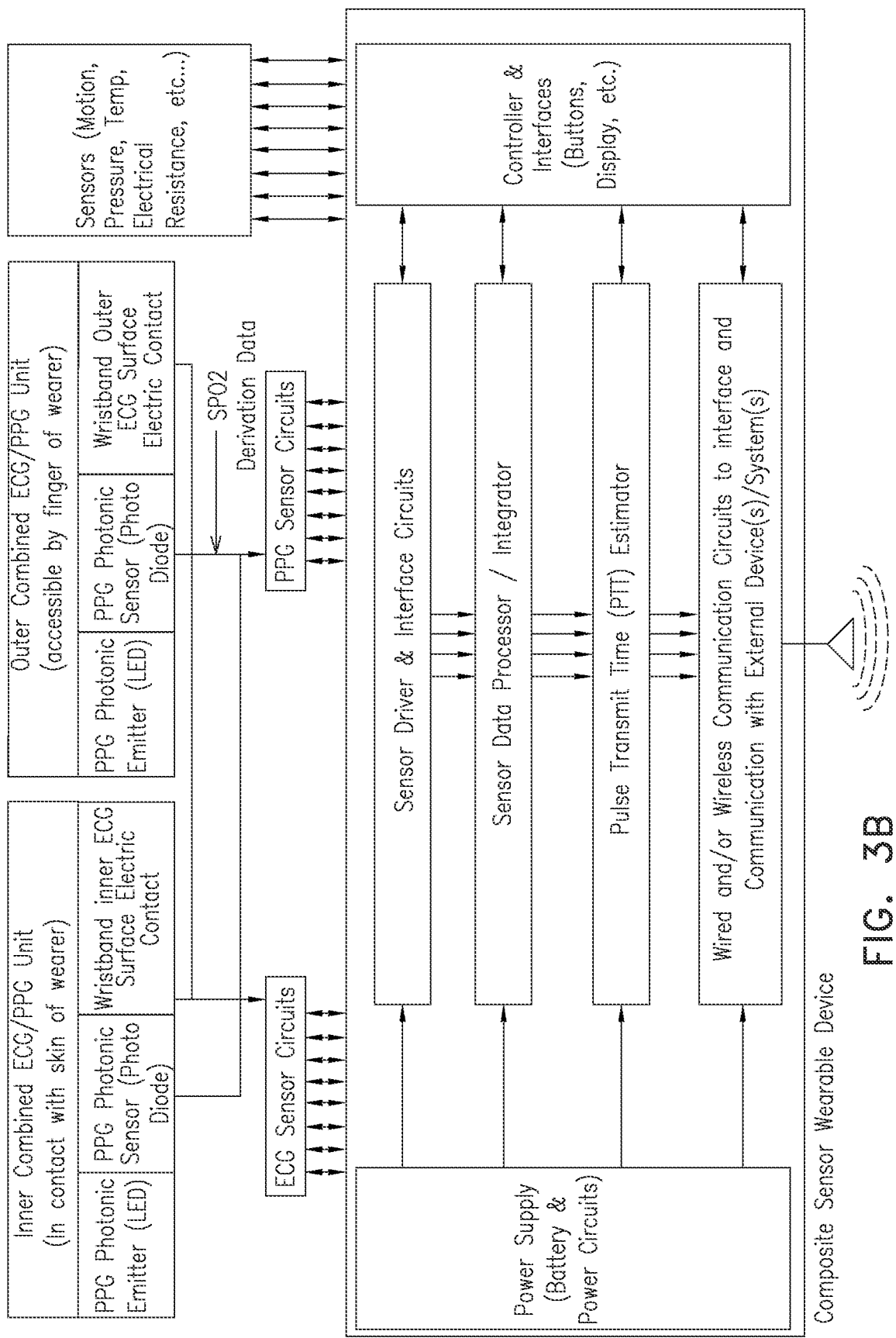
FIG. 3B, is a functional block diagram of an exemplary wearable device, including two combined ECG/PPG Units, an inner one and an outer one, in accordance with some embodiments of the present invention.

In FIG. 3B, there is shown a functional block diagram of an exemplary wearable device, in accordance with some embodiments of the present invention, wherein the device includes two combined ECG/PPG Units, an inner one and an outer one, and wherein the outer unit is accessible by a finger of a wearer of the device (e.g., a finger of the hand opposite to the hand on which a wristband/watchband device is worn). The outer unit accordingly acts as a second ECG electrode/electrode-batch/contact/lead; and as a second PPG sensor, accessible by the finger of the device wearer, thus enabling the measurement, or substantially accurate measurement, of his SPO2. The combined outer unit, in accordance with embodiments, measures ECG signals and SPO2 levels simultaneously while the device wearer is placing his finger and making contact with the outer unit.

Figure 4:
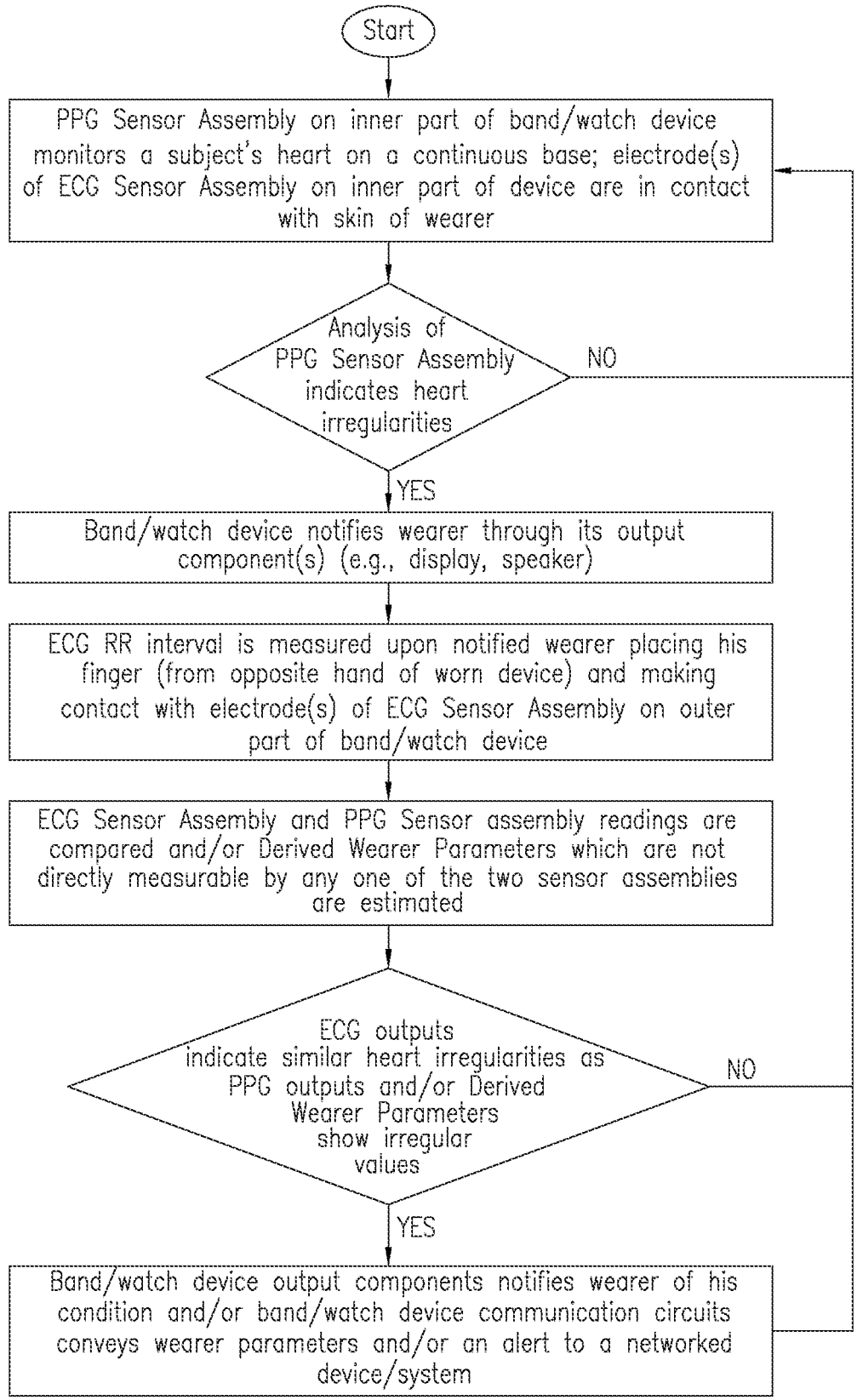
FIG. 4, is a flowchart of the process and main steps executed by a composite sensor wearable device, in accordance with some embodiments of the present invention, as part of an exemplary diagnostic embodiment.

In FIG. 4, there is shown a flowchart of the process and main steps executed by a composite sensor wearable device, in accordance with some embodiments of the present invention, as part of an exemplary diagnostic embodiment.

Figure 5:
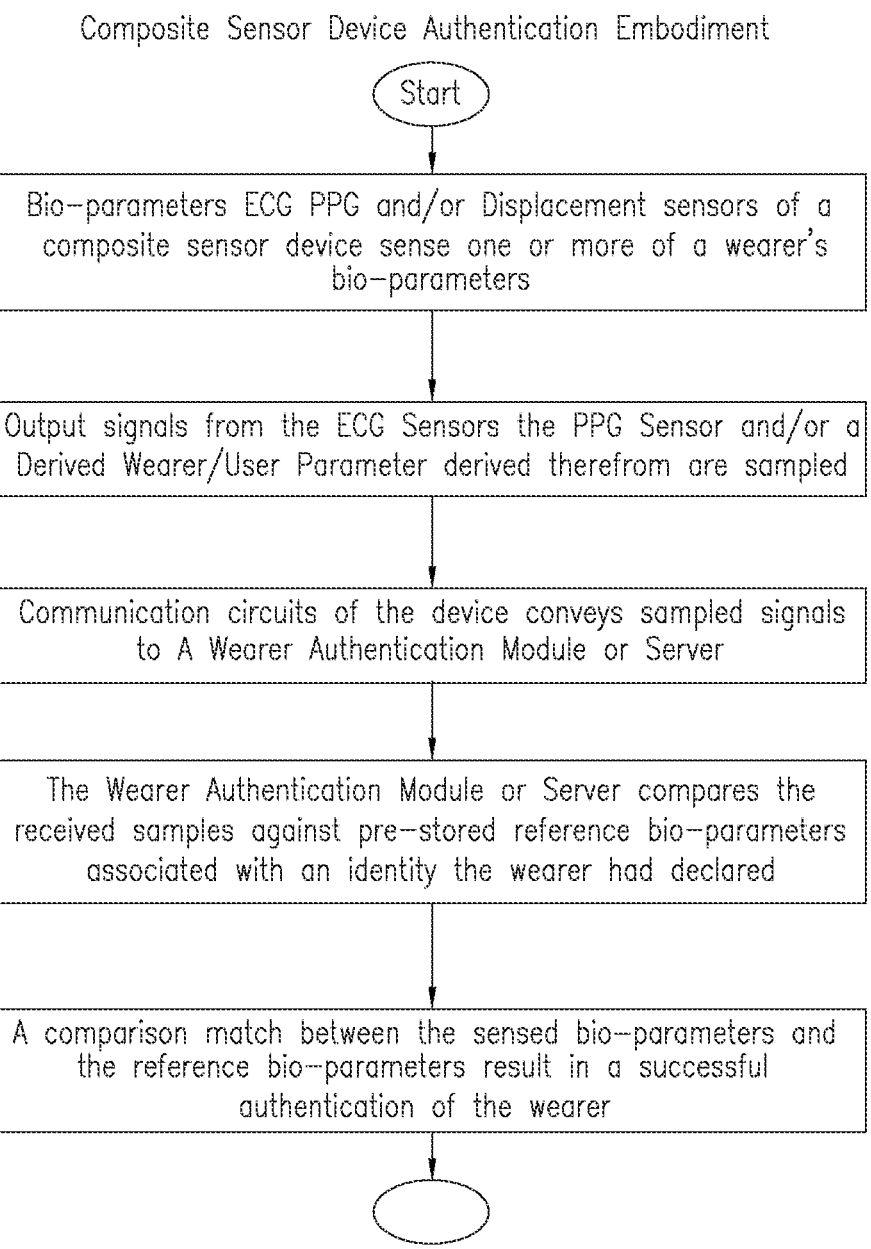
FIG. 5, is a flowchart of the process and main steps executed by a composite sensor wearable device, in accordance with some embodiments of the present invention, as part of an exemplary authentication embodiment.

In FIG. 5, there is shown a flowchart of the process and main steps executed by a composite sensor wearable device, in accordance with some embodiments of the present invention, as part of an exemplary authentication embodiment.

Figure 6:
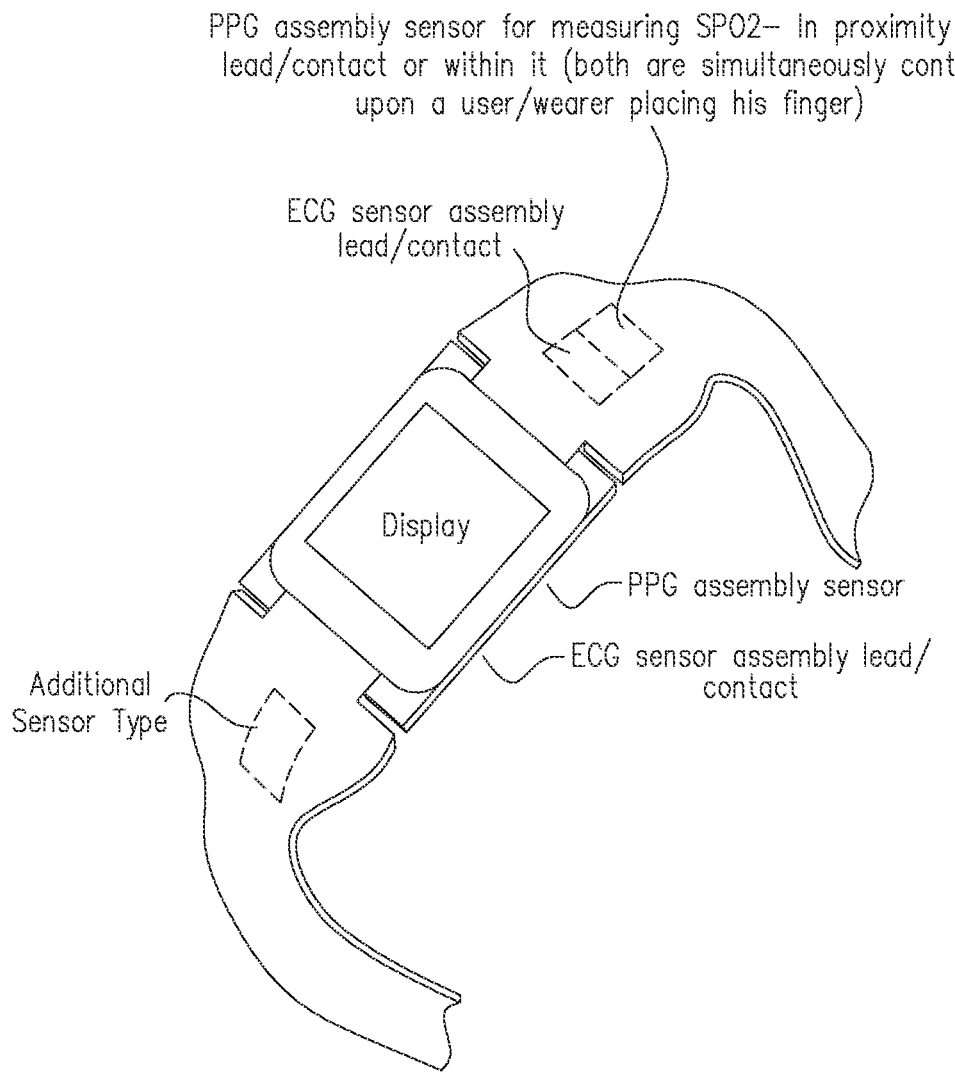
FIG. 6, shows, in accordance with some embodiments of the present invention, an exemplary composite sensor device with a wristwatch form factor.

In FIG. 6, there is shown, in accordance with some embodiments of the present invention, an exemplary device with a wristwatch form factor. The embodiment shown in FIG. 6 also includes contacts for an ECG sensor assembly visible on the outer side of the watchband wherein the location of a first ECG lead or contact of the ECG assembly is shown. The location of a second ECG lead or contact, placed on the inner or back surface of the watchband, is also pointed to. Also pointed to are the PPG assembly sensors which are located on the inner surface of the wristwatch band.

When a user/wearer straps the wristwatch band on their arm wrist, the PPG sensors and ECG lead come in contact and touch the wearer's wrist. The first ECG lead/contact, which is located on an outer surface of the watchband, can be touched by a finger or palm of the wearer's other hand. In proximity to the outer ECG lead/contact or within it, such that both are simultaneously contacted upon a user/wearer placing his finger, an additional, outer, PPG assembly sensor is shown, for measuring SPO2 of the wearer (i.e. from his contacting finger).

Alternatively, the first ECG lead/contact can be placed in contact with the chest of the wearer. The configuration of FIG. 6 allows for the measurement of ECG and PPG signals at the same time, which in turn may allow for the estimation of the Pulse Transmit Time (PTT). The configuration of FIG. 6 also including the outer, wearer finger contactable, PPG sensor allows for the measurement of SPO2.

An additional sensor type shown may be anyone of several different sensor types, including, but not limited to: an SPO2 sensor, a capacitance sensor, a galvanic sensor and/or others. The above sensors can be used as either main or supporting sensors that work together with a finger print sensor. According to additional embodiments the additional sensor may be a fingerprint sensor. Further shown is the display of the wristwatch for presenting sensors associated data, wearer bio-parameters derived therefrom, and/or associated notifications.

Figure 7:
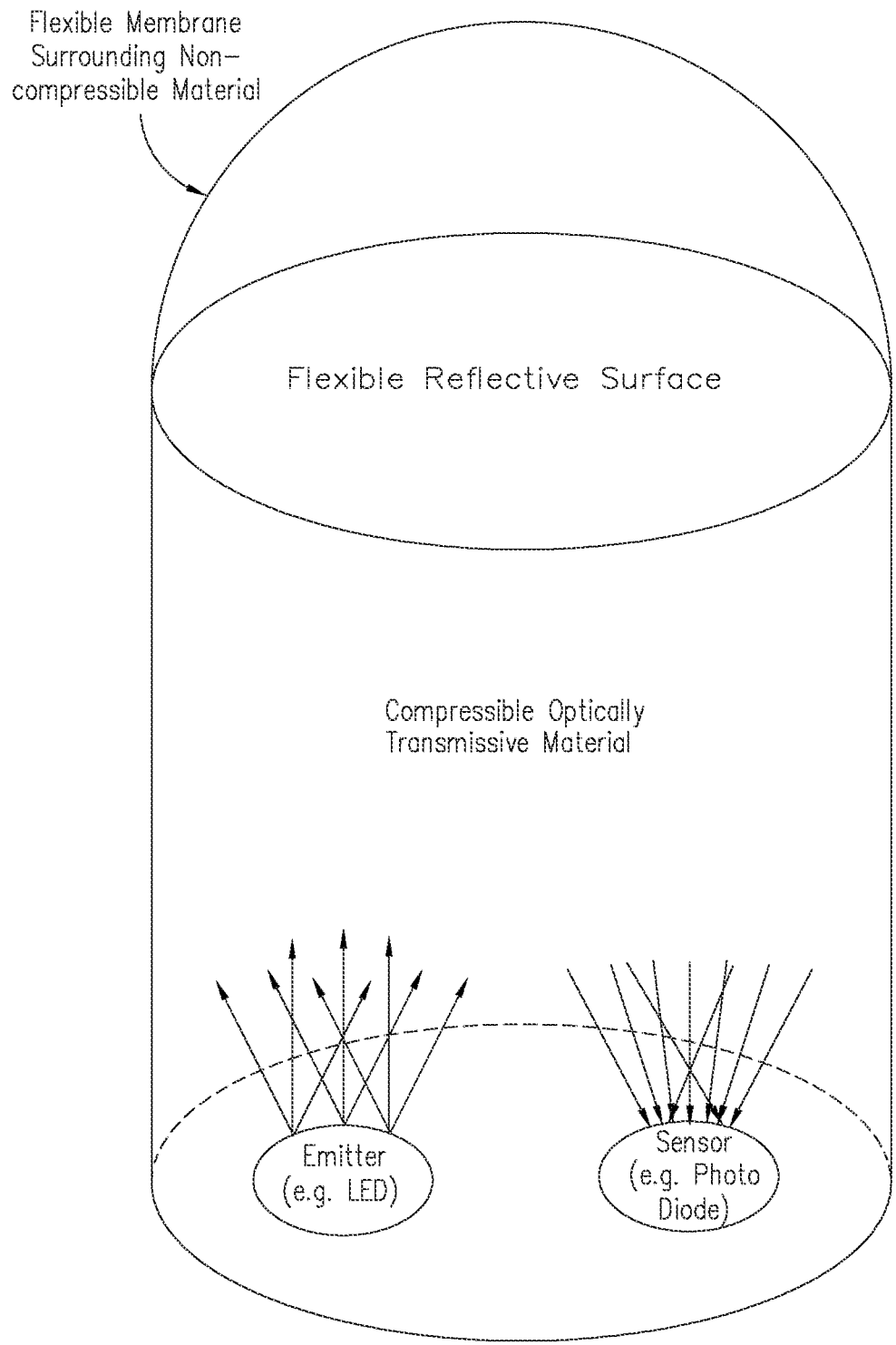
In FIG. 7, there is shown, in accordance with some embodiments of the present invention, an exemplary PPG sensor integrated with a Pressure Sensor.

In FIG. 7, there is shown, in accordance with some embodiments of the present invention, an exemplary PPG sensor integrated with a Pressure Sensor. The PPG/Pressure Sensors shown, include an upper section made of a Flexible Membrane Surrounding a Non-Compressible Material, for making contact with a body part of a subject (e.g., the finger of a wearer of a composite sensor watch/band). Further shown is a lower section made of a Compressible Optically Transmissive Material for absorbing pressure induced by contact made by the body part of the subject (e.g., finger skin) and providing respective pressure indicative signals. The Optically Transmissive Material of the lower section allows for the functionality of the PPG sensing elements, namely the passage of light from the shown Emitter to reach the body part of the subject (e.g., finger skin), and to at least partially reflect back to the shown Sensor Photo Diode generating respective PPG signals. Pressure indicative signals may be used to compensate for and thus mitigate PPG sensing artifacts, which artifacts may be at least partially due to change of pressure the PPG sensor(s) feels with relation to the skin.

Figure 8A:
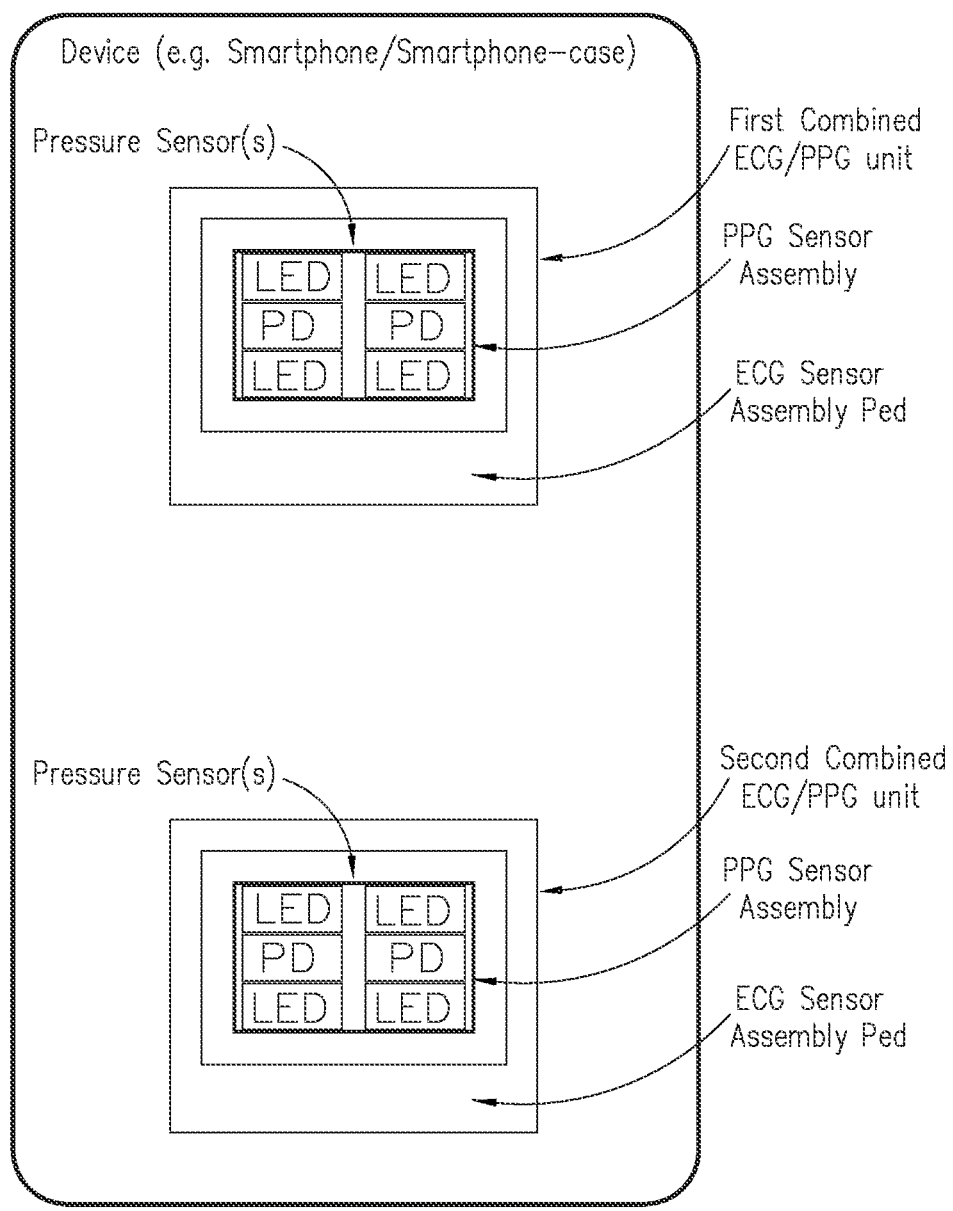
In FIGS. 8A-8D, there are shown, in accordance with some embodiments of the present invention, exemplary device including composite sensor units.
Figure 8B:
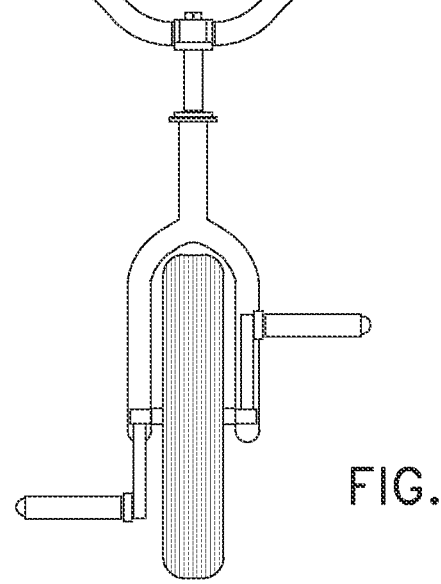

In FIGS. 8A-8D, there are shown, in accordance with some embodiments of the present invention, exemplary device including composite sensor units. In FIG. 8A there is shown a device (e.g., a smartphone) or device case on which two Combined ECG/PPG Units are positioned. Each of the Combined ECG/PPG Units shown includes: a PPG Sensor Assembly comprising LEDs to emit light and Photo Diodes (PDs) to generate signals based on light emitted by the LEDs and reflected from the skin of a subject. The PPG Sensor Assembly is integrated-into/positioned-within a Pressure Sensor(s) used for mitigating PPG sensing artifacts. The Pressure Sensor(s) and its hosted PPG Sensor Assembly are collectively positioned within/substantially at the center of (according to some embodiments may also be positioned adjacent to) an ECG Sensor Assembly Pad. Accordingly a subject/user/wearer of the device may make contact with all three sensors—ECG, PPG, and Pressure—as part of a single contact generating touch of the Combined Unit.

Figure 8C:
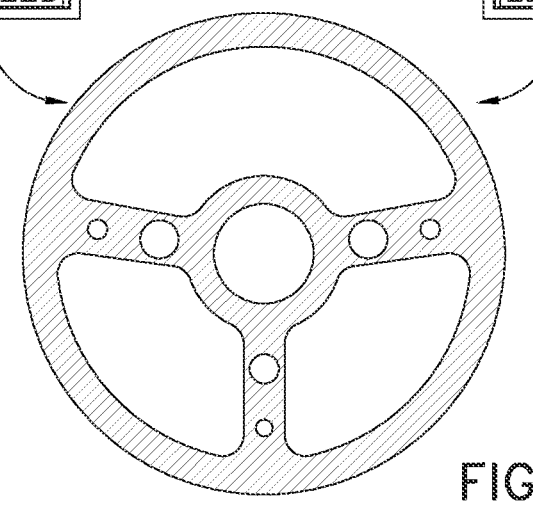
Figure 8D:
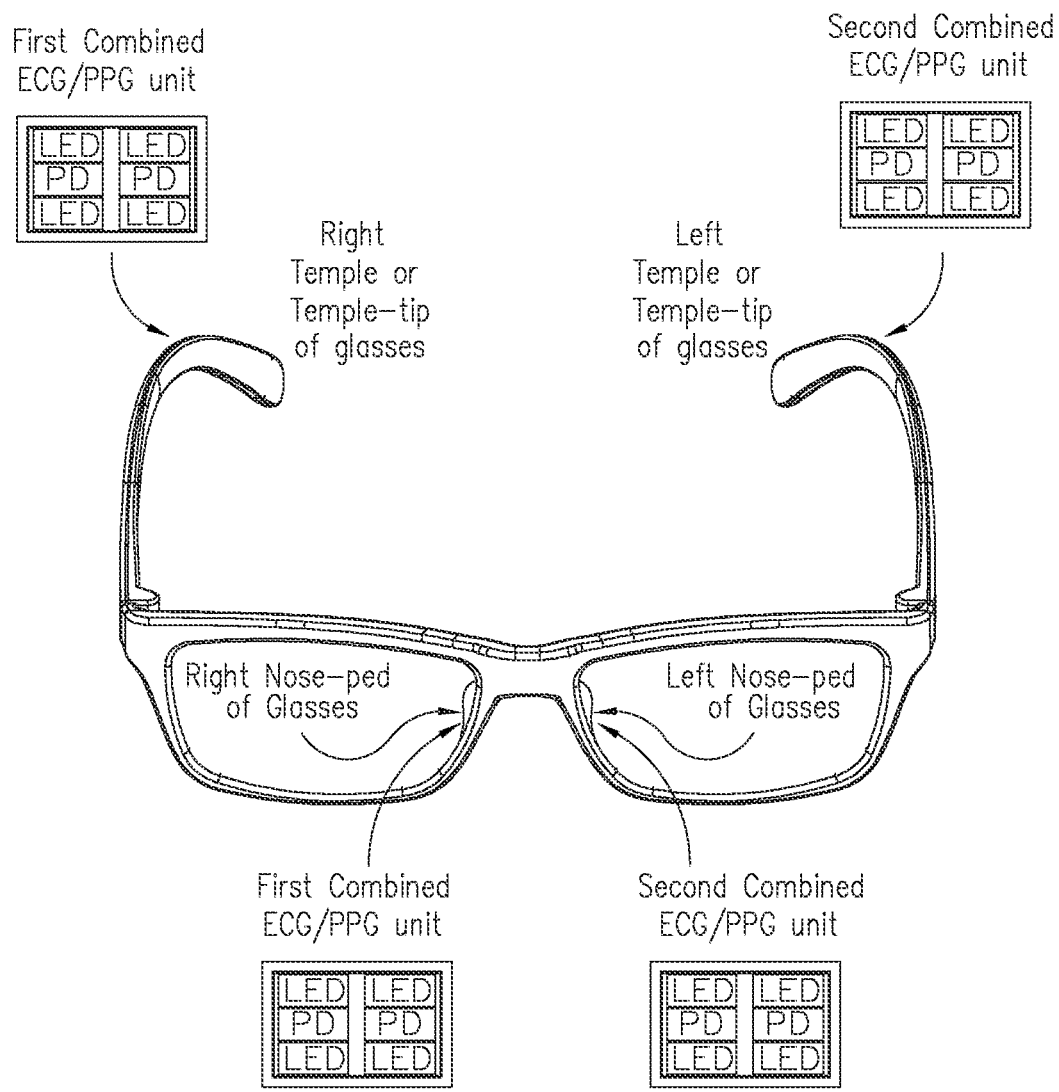

In FIGS. 8C-8D, there are shown, in accordance with some embodiments of the present invention, additional exemplary devices including composite sensor units. There are shown: composite sensor units on the handlebars of a bicycle (FIG. 8B), composite sensor units on the top right and top left sections of a steering wheel (FIG. 8C), and composite sensor units on the temples, temple-tips, or nose-pads of a pair of glasses (FIG. 8D).

Figure 9:
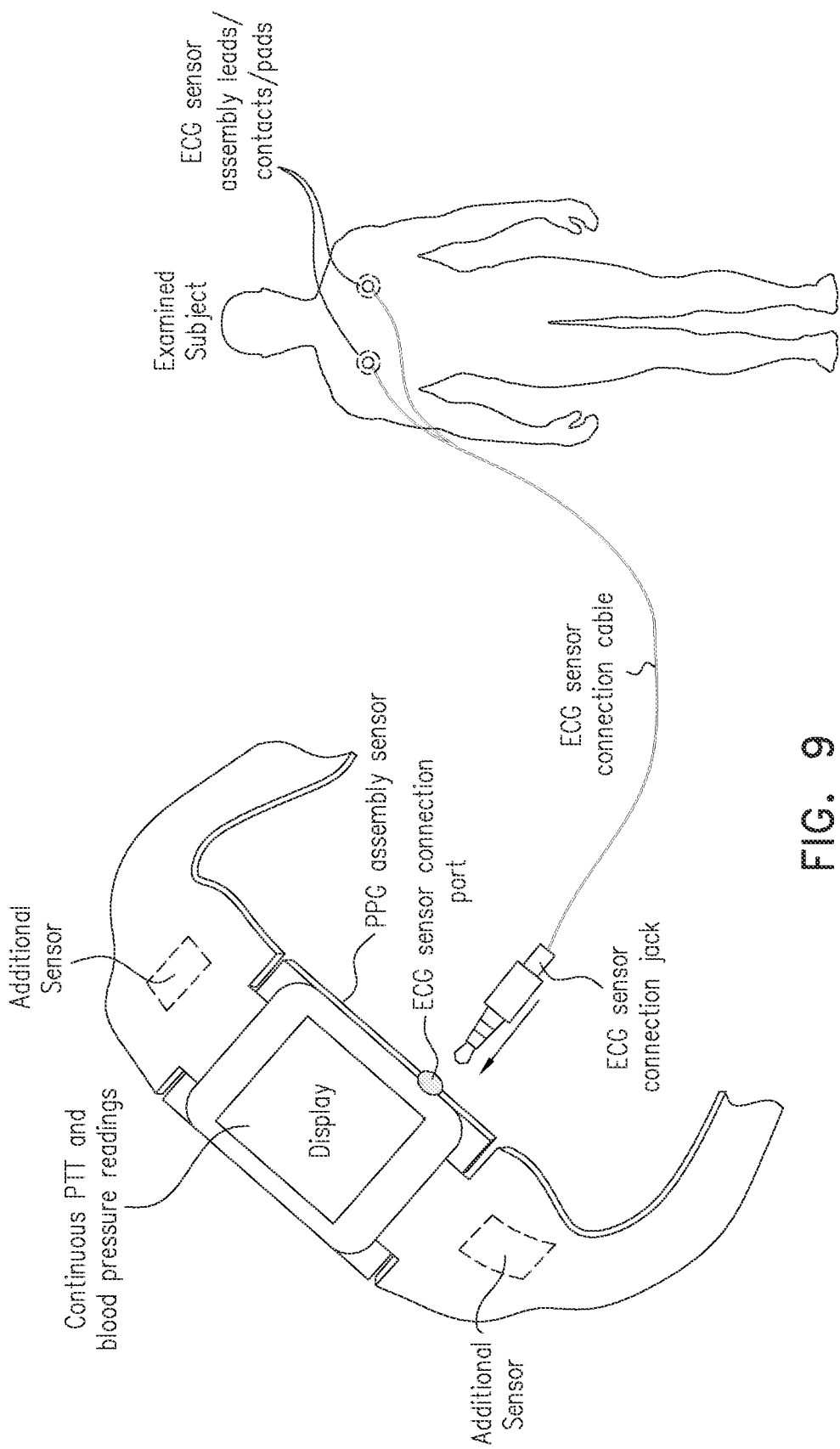

In FIG. 9, there is shown, in accordance with some embodiments of the present invention, an exemplary wearable device incorporating a composite sensor assembly(s) combining ECG type, PPG type, and/or Pressure/Motion type sensors. The device shown provides continuous monitoring of PTT. In the figure, there is shown, A Connection Port on the side of the body of the device for accepting the shown Connection Jack. Two ECG Pads are shown connected to two sides of a subject's chest while collectively and continuously monitoring ECG signals from the subject's heart. The Connection Cable shown connects between, and carries ECG signals between, the two ECG Pads on the subject's chest and the connection jack on the device side. Based on the continuously monitored ECG signals provided through the connection jack and port, when combined with continuously monitored PPG signals provided by the PPG sensor pointed to in the figure, at the bottom of the wearable device, continuous PTT readings, and thus continuous blood pressure readings of the device using/wearing subject, are generated by the processing circuits/circuitry/logic (not shown in figure) and presented on the display of the device.

Further Embodiments

According to some embodiments of the present invention, a composite bio-parameter sensor assembly for detecting one or more biological parameters of a subject person, may comprise: a first sensor, of a first sensor type, having a first sensing surface to optically detect one or more parameters of a pulse of a subject; and/or a second sensor, of a second sensor type, having a second sensing surface to electrically detect one or more parameters of a pulse of a subject and substantially aligned with the first sensing surface of the first sensor, such that a subject touching the assembly concurrently comes in contact with the first sensing surface and the second sensing surface. According to some embodiments, the first sensing surface may be either adjacent to, or surrounded by, the second sensing surface.

According to some embodiments, the first sensor may be a PPG sensor, the second sensor may be an ECG sensor, and the assembly may further comprise: (a) a pressure sensor to detect pressure waves passing through skin of the subject, and (b) circuitry to compensate for artifacts within the PPG signal due to pressure waves.

According to some embodiments, the sensor assembly may further comprise control and circuit processing circuits to operate the sensors, process signals produced by the sensors, and/or to derive biological parameters from sensor signals.

According to some embodiments, operation of the first and second sensors may be coordinated by the controller in accordance with an operational scenario. The operation of the first PPG sensor and second ECG sensor may be triggered as a result of a user touching a sensing surface.

According to some embodiments, biological parameters detected by the PPG sensor, the ECG sensor, and/or by a combination of data from both the PPG and ECG sensors, may include, but is not limited to: Heart Rate, Heart Rate Variability, Breathing Rate, ECG signal, Pulse Transmit Time, Blood Pressure, Heart arrhythmias, and Oxygen saturation. According to some embodiments, biological parameters sensed by the sensors may be used for: (a) health monitoring, (b) subject identification, (c) subject authentication, (d) medical diagnostics, (e) human machine interfacing.

According to some embodiments of the present invention, a composite sensor device for detecting one or more biological parameters of a subject person, may include at least a first and a second composite bio-parameter sensor assemblies. Each of the assemblies may comprise: a first sensor, of a first sensor type, having a first sensing surface to optically detect one or more parameters of a pulse of a subject; and/or a second sensor, of a second sensor type, having a second sensing surface to electrically detect one or more parameters of a pulse of a subject and substantially aligned with the first sensing surface of the first sensor, such that a subject touching one of the assemblies concurrently comes in contact with its first sensing surface and said second sensing surface.

According to some embodiments, the first sensor, of each of the assemblies, may be a PPG sensor, the second sensor, of each of said assemblies, may be an ECG sensor. Each of the assemblies may further comprise: (1) a pressure sensor to detect pressure waves passing through skin of the subject, and (2) circuitry to compensate for artifacts within the PPG signal due to pressure waves.

According to some embodiments, the composite sensor device may have a wristwatch or wristband form factor, and the first sensor assembly may be part of an inner section of the wristwatch or wristband device and the second sensor assembly may be part of an outer side of the wristwatch or wristband device.

According to some embodiments, the first assembly, of a composite sensor device, may be part of a user's designated right hand holding position of the device, and the second assembly, of the composite sensor device, may be part of a user's designated left hand holding position of the device. According to some embodiments, the type of a composite sensor device may be, but is not limited to: a bicycle, a motorcycle, a wheelchair, a bed, a treadmill, an exercising machine, a handlebar, handlebars, a steering wheel, a weapon, a work tool, a house tool and a kitchen tool.

According to some embodiments, the composite sensor device may further comprise control and circuit processing circuits to operate the sensors of the assemblies, process signals produced by the sensors of the assemblies, and/or to derive biological parameters from the sensor signals.

According to some embodiments, the operation of the first and second sensors, of each of the assemblies, may be coordinated by the controller in accordance with an operational scenario. According to some embodiments, the operation of at least one, of the first and second sensors of both the assemblies, may be triggered as a result of a user touching a sensing surface of the first assembly and a sensing surface of the second assembly.

According to some embodiments, biological parameters detected by the PPG sensors, the ECG sensors, or by a combination of data from both the PPG and ECG sensors, may include, but is not limited to: Heart Rate, Heart Rate Variability, Breathing Rate, ECG signal, Pulse Transmit Time, Blood Pressure, Heart arrhythmias, and Oxygen saturation.

According to some embodiments, the first sensing surface of the first assembly, may be either adjacent to, or surrounded by, the second sensing surface of the first assembly; and/or the first sensing surface of the second assembly, may be either adjacent to, or surrounded by, the second sensing surface of the second assembly.

According to some embodiments of the present invention, a composite sensor device for continuous monitoring the PTT of a subject person, may comprise: a first sensor, of a PPG sensor type, to continuously optically detect one or more parameters of a pulse of the subject; a second sensor, of an ECG sensor type, having two or more ECG pads connectable to two sides of the body of the subject, to continuously electrically detect one or more parameters of a pulse of the subject; a connection port on the body of the composite sensor device; a connection cable for carrying ECG signals between the two or more ECG pads and a connection jack connected to the connection port; and/or processing circuits for generating continuous PTT readings and/or continuous blood pressure readings of the device using/wearing subject, based on the continuously monitored ECG signals provided by the second sensor, of an ECG sensor type, through the connection port, when combined with continuously monitored PPG signals monitored by the first sensor, of a PPG sensor type.

By using optical means, a measurement of a biological parameter, e.g., heart rate or heart rate variability, from a surface of the skin such as the wrist, can be obtained. In order to determine a biological parameter indicative of the heart rate, the skin is illuminated with an illumination having a wavelength characterized by that it (i) can penetrate through the skin; (ii) absorbed by blood components, in particularly oxygenated hemoglobin; and (iii) has a penetration depth suitable to penetrate the epidermis and to interact with the blood components in the papillary region of the dermis adjacent to the epidermis (with minimum interaction with the reticular region of the dermis).

Figure 10:
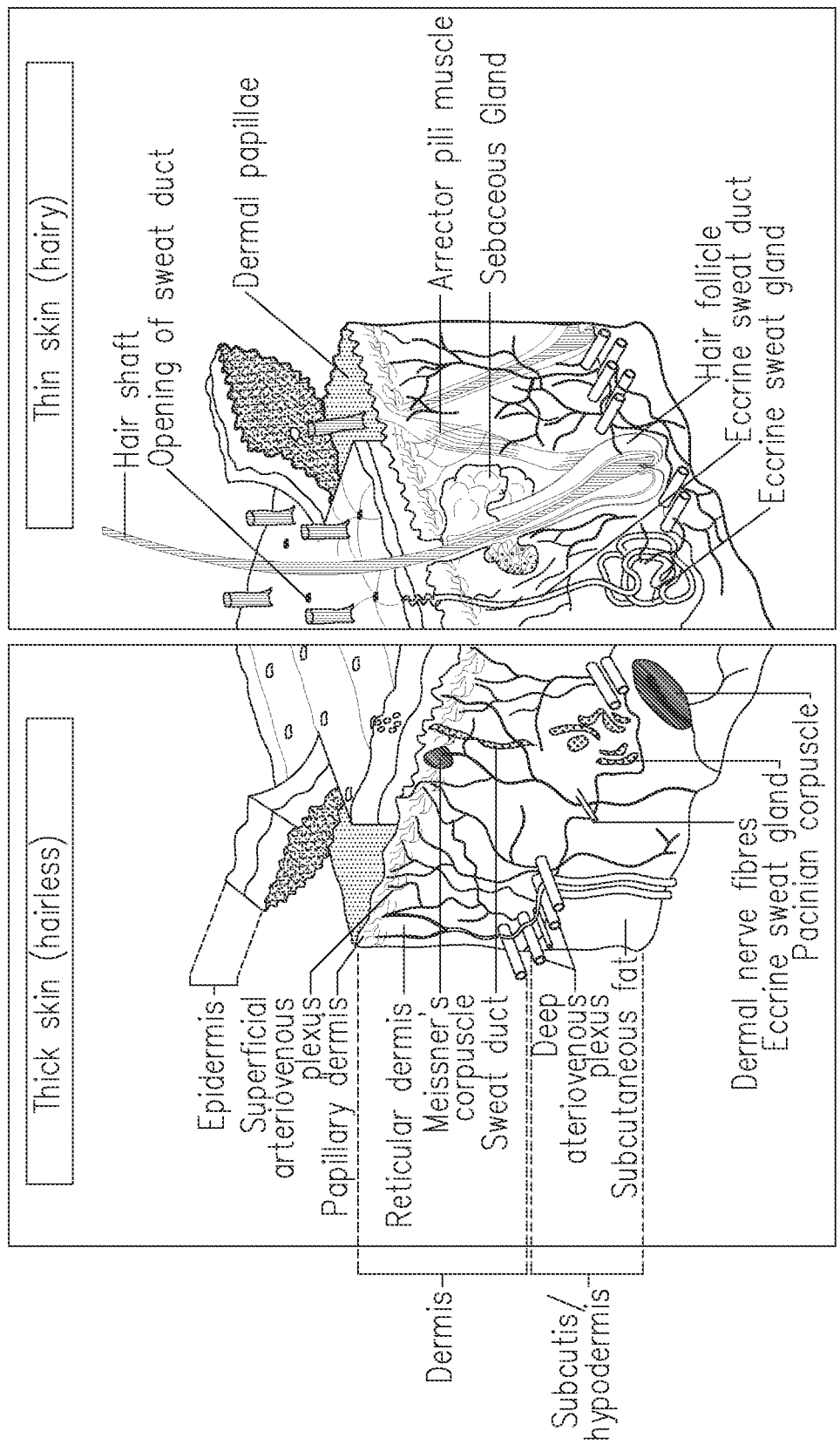
FIG. 10 is a schematic illustration of a longitudinal cross section of a hairy and hairless skin portion of a human subject, exemplifying the layers of the skin.

As can be seen in FIG. 10, whether it is a hairless or hairy portion of the skin, the first outer layer of the skin is the epidermis, that forms a barrier to infection from environmental pathogens and regulates the amount of water released from the body into the atmosphere through transepidermal water loss. The thickness of the epidermis varies between 0.05 mm and 1.5 mm Under the epidermis layer, is the dermis layer having a thickness of between 1.5 mm and 4 mm making up approximately 90 percent of the thickness of the skin. The dermis is divided into two main layers, the more outer layer, the papillary dermis which is adjacent to the epidermis; and the reticular dermis which is a deeper layer following the papillary dermis. The papillary region of the dermis is the region of interest since it is dense with blood vessels, and the data of illumination response collected therefrom may be indicative of heart rate, hear rate variability breathing rate, oxygen saturation and more.

The visible light spectrum provides wavelengths having the above mentioned characteristics, such as wavelength in the green spectrum (between 520 nm and 540-nm) and in the violet spectrum (between 405 nm and 430 nm). However, when illuminating (e.g., with LEDs) a skin of a subject with illumination having one of the above wavelengths, a non-negligible amount of the illuminated light may penetrate deeper than the papillary region, interacts with the reticular region, and does not contribute to the relevant data that is indicative of the biological parameters (such as heart rate).

Thus, another aspect of the present disclosure provides a device for sensing at least one biological parameter (e.g., heart rate, heart rate variability) of a subject, in which the optical path of an illumination within the papillary dermis of the subject is extended. In other words, the device of the present disclosure provides a configuration in which an illumination from a light source, such as a LED source, is directed to the skin in such a way that the illuminated light will interact substantially with the papillary region of the dermis rather than the reticular region of the dermis and layers below it (such as the Subcutaneous layer).

To this end, the device has at least one light source for illuminating the surface through a contact surface, configured to be in contact with measured skin surface, and at least one detector for detecting a response of said illumination through the contact surface. A response can be any kind of reflection, whether it is a total reflection or a diffusive reflection derived from a blood component or other part of a measured tissue. While the device is in operation, namely, while the device is positioned in contact with the skin, the light source is configured to be tilted with respect to the contact surface, therefore, also angled with the skin it illuminates. In other words, the illumination optical axis of the light source is angled with respect to the surface of the skin. The acute angle between the illumination optical axis of the light source and the contact surface can vary between 1 to 89 degrees, preferably between 10 to 80 degrees, more preferably between 30 to 60 degrees.

In some embodiments, the at least one light source and the at least one detector may be fixedly attached on a single surface, sensors' surface, spanning a plane. The light source may be tilted with respect to a plane spanned by such a surface, namely the acute angle between the illumination optical axis of the light source and the sensors' surface can vary between 1 to 89 degrees, preferably between 10 to 80 degrees, more preferably between 30 to 60 degrees.

Yet, in some other embodiments, the contact surface is formed on a barrier member extending from the sensors' surface and confining the at least one light source and the at least one detector within a void therein. The barrier member provides a barrier between the measured skin surface, and the light source and detector, thus protecting them.

The sensing device can be implemented in a wearable device, in particular one that is worn on the wrist. The contact surface of the barrier member is configured to contact the measured skin surface portion while the measurement is carried out, namely the wrist skin is illuminated and the response of the illumination is detected by the detector.

Figure 11A:
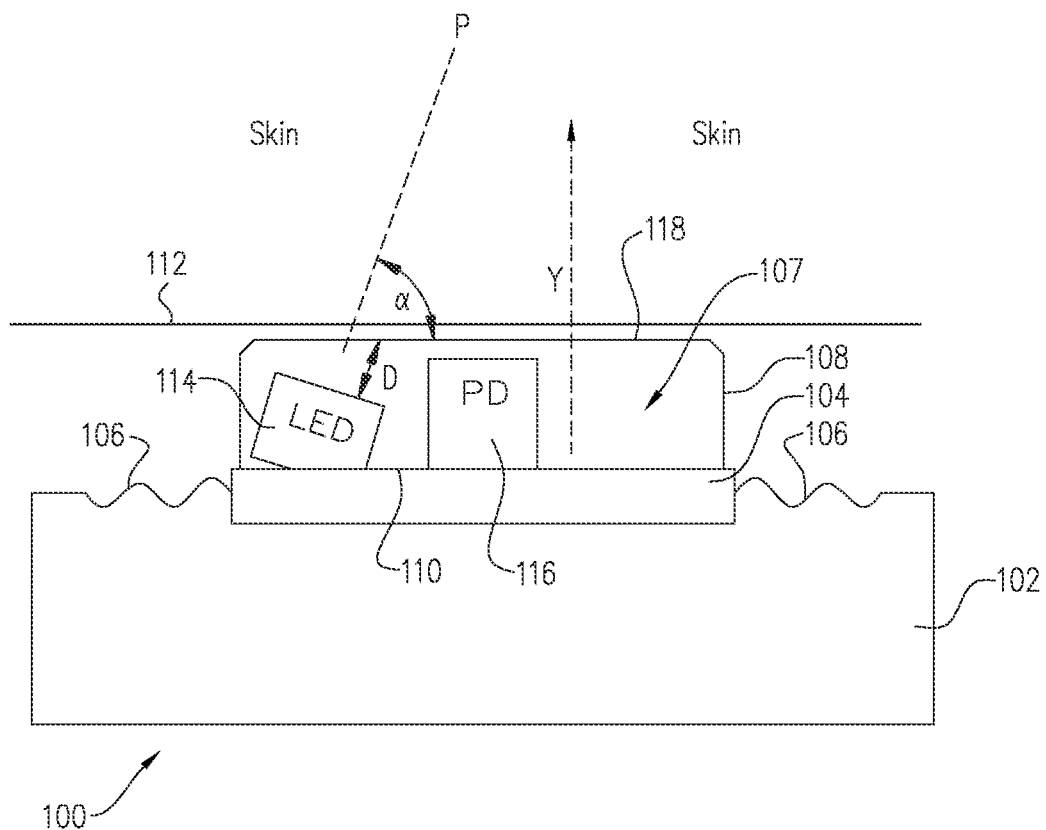
FIGS. 11A-11B are schematic illustrations of a longitudinal cross section of embodiments of a device of an aspect of present disclosure.
Figure 11B:
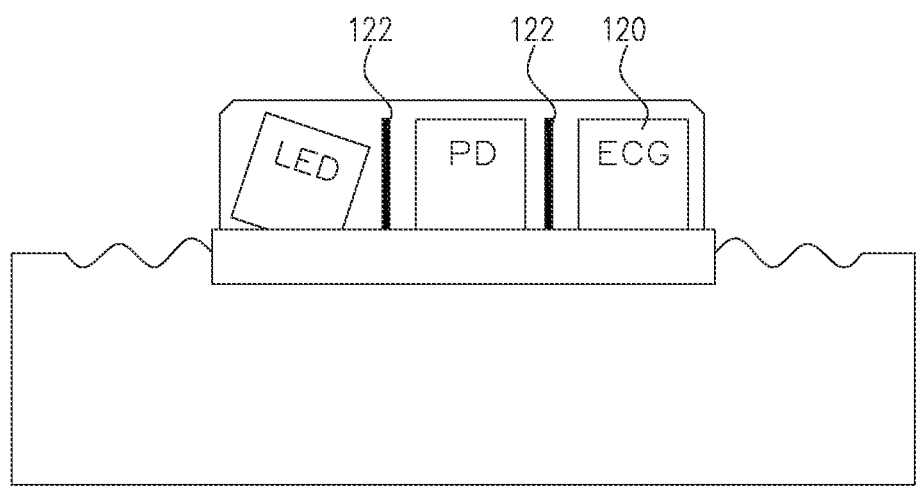

FIG. 11A-11B are schematic illustrations of embodiments of a device for sensing at least one biological parameter of a subject. The device 100 has a housing 102 coupled to a substrate 104 by two flexible members 106 (e.g., a flexible membrane, a spring). The flexible members 106 have elastic properties allowing movement of the sensors' surface 104 with respect to the housing 102 when force is applied on the substrate 104 directly or through a force applied on a barrier surface 108 that is confining components of the device in its inner void 107 defined between its periphery surface 109 and a sensors' surface 110. The movement allowed by the flexible member 106 is particularly important in the direction perpendicular the substrate 104 as shown by arrow Y. The flexible movement of the substrate 104 and the components attached thereto, reduces the pressure applied by the barrier surface 108 on the measured skin surface 112, thereby reducing undesired effects in the measurement of the blood. When the pressure applied on the skin rises, it may change the natural flow of the blood as well as flow of other tissue elements such as the extracellular, therefore the measurement of the blood components by such a device will be less accurate. The substrate 104 comprising a Printed Circuit Board (PCB), to which the sensors are attached. In this example, a PPG sensor is attached to the substrate 104, the PPG sensor comprising a light source, a LED 114 and a photodiode (PD) detector 116. The LED 114 is tilted, such that its optical axis P is angled with respect to the contact surface 118 in an acute angle of a degrees. In this example, the principle axis P of the LED 114 is tilted in the same angle α also with respect to the sensors' surface 110 of the substrate 104 and to a contact surface 118 of the barrier surface 108 that is in contact with the measured skin during operation of a measurement. In other words, the sensors' surface 110, the contact surface 118 and the measured skin 112, when is brought in contact with the device during measurement, span generally parallel planes.

the device 100 has a pre-determined operational distance D from the contact surface, such that at a distance exceeding said operational distance D said response at said wavelength is essentially lower than at a distance not exceeding said operational distance D.

As shown in FIG. 11B, an ECG electrode 120 can be attached to the substrate 104 and together with another electrode (not shown) comprised in the device can measure ECG parameters in addition to the parameters obtained by the PPG sensor.

A buffer 122 is surrounding the PD obstructs light that is not reflected from the skin 116, thereby prevents a detection of light that is considered as "noise".

The device of the present disclosure may have more than one light source, thereby increasing the accuracy of the measurements. Multiple light sources may be configured around a detector so as to illuminate the skin from different angles, (i) increasing the intensity of the illumination, and (ii) reducing statistical error probability in case a single light source illuminating from a single direction. Furthermore, each of the multiple light sources can illuminate with different wavelength. As skin color may affect the penetration depth of a certain wavelength through the skin, in particularly through the epidermis, the use of illumination with different wavelengths will be useful to penetrate through both dark and bright skin. It is also noted, that different wavelengths have different penetration depths in the dermis layer. Reduction of penetration depth enable most of the light to penetrate the skin up to the end of the papillary dermis and by that improve measurement dramatically.

Figure 12:
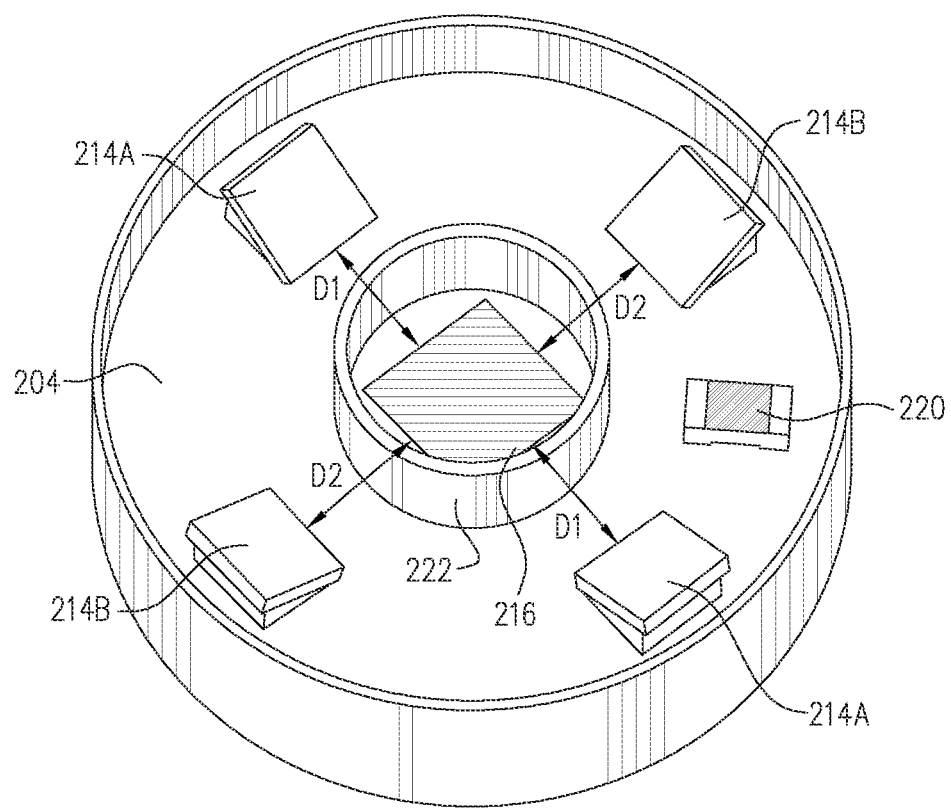
FIG. 12 is an isomeric schematic illustration of an exemplary configuration of LEDs around the photodiode of the device of an aspect of the present disclosure.

FIG. 12 is an isometric view of sensors' surface of another embodiment of the device of the present disclosure, exemplifying a configuration of multiple LED light sources around a PD detector. The PD 216 is located at the center of the substrate 204 surrounded by buffer 222. Two pairs of LEDs 214A, 214B, disposed in opposite sides of the sensors' surface 204, the PD 216 disposed between an axis connecting each pair. Each of the LEDs is tilted with respect to the substrate 204 facing towards the center of the substrate 204 and the PD 216. The LEDs 214A are illuminate with a first wavelength, for example a wavelength in the green spectrum, and the LEDs 214B illuminate with a second wavelength, for example a wavelength in the violet spectrum. Since the penetration depth in the skin depends in the wavelength, the LEDs 214A, 214B are disposed in distances D1, D2, respectively, with respect to the PD 216 such that the reflected light from the blood components in the skin received in the PD 216 is optimal. The distances D1 and D2 are also affected by the tilted angle of the LED light sources 214A and 214B with respect to the substrate 204 or to a contact surface (not shown). Also in this example, an ECG electrode 220 is attached to the substrate 204.

The accuracy of the biological parameters measurements is affected by movements of the measured surface, known as artifacts effects. For example, if the measurement is taken from a skin surface of the wrist, a movement of the hand or the fingers may affect the accuracy of the measurement.

Another aspect of the present disclosure provides an artifact, movement sensor for detecting movement of the measured skin surface.

The sensor has a substrate having or rigidly integrate with a contact surface for contacting the measured skin surface and sensors' surface facing to an opposite side to the contact surface. At least one light source and at least one detector are fixedly attached to the sensors' surface.

The substrate is coupled to a housing of the sensor by at least one flexible member in a manner to permit the substrate and the contact surface to move at least in a direction perpendicular to the contact surface.

The light source is configured to illuminate a reflection surface formed or fixed in the housing, and the detector is configured to detect at least the illumination reflected from the reflection surface. The reflection surface is fixed to the housing such that a movement of the substrate does not impose any movement thereof.

The intensity of detected light from the reflection surface is indicative of the position of the substrate with respect to the reflection surface. The deflection of the substrate from its steady state is indicative of the pressure being applied on the substrate, such as pressure applied by measured skin portion coming into contact with the contact surface.

Figure 13A:
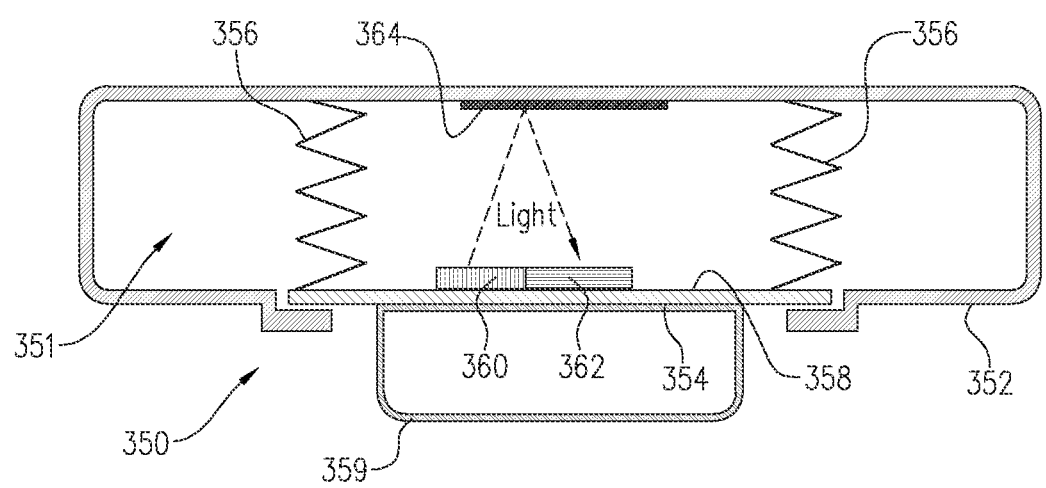
FIGS. 13A-13B are schematic illustrations of an embodiment of a movement sensor of an aspect of the present disclosure.
Figure 13B:
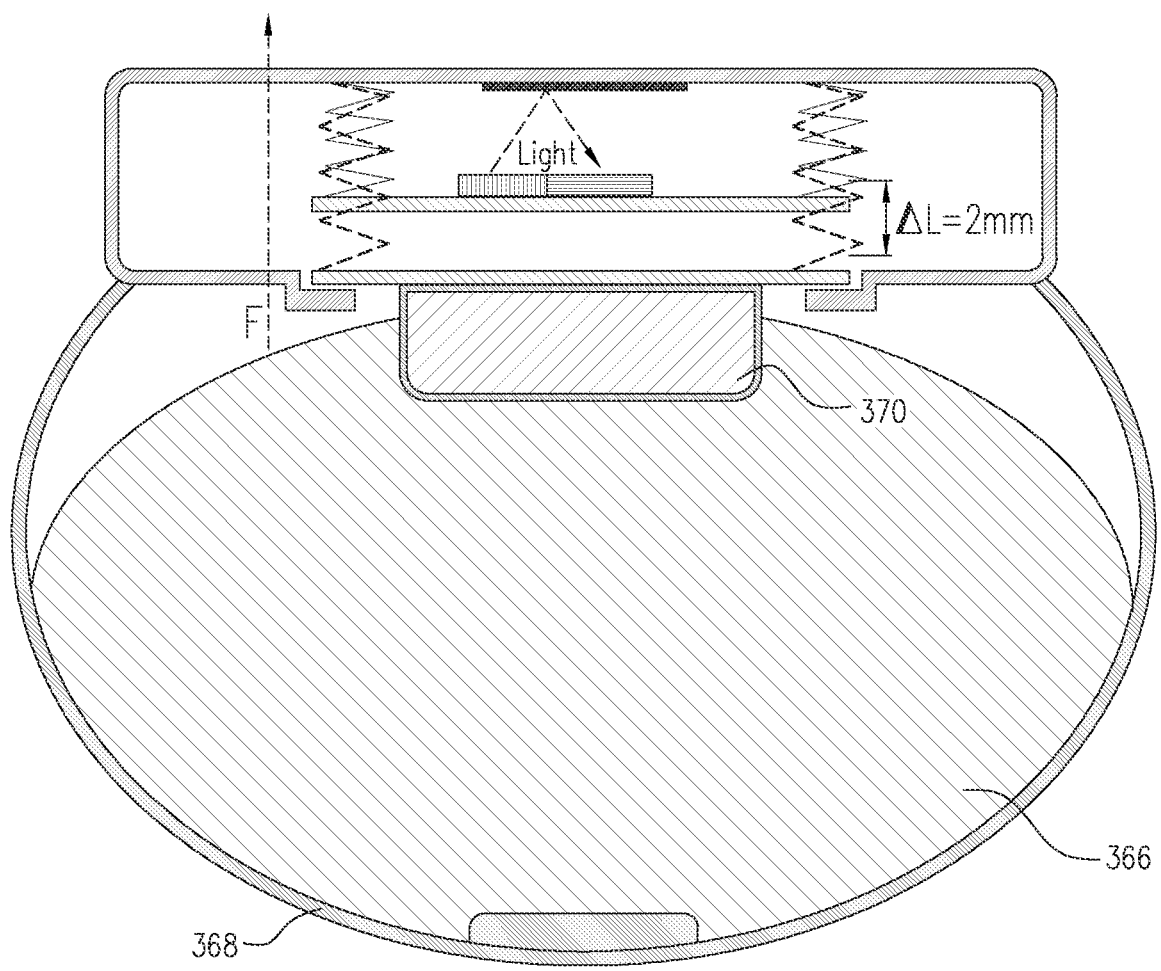

FIG. 13A shows a schematic illustration of a longitudinal cross section of an embodiment of a sensor according to this aspect of the disclosure. A sensor 350 with a housing 352 with an inner cavity 351 is coupled to a substrate 354 by two flexible members 356 in the form of springs. The substrate has a sensors' surface 358 facing to the inner cavity 351 on which a LED light source 360 and a photodiode detector 362 are fixedly attached. A contact surface 359 is rigidly integrated with the substrate 354 facing an opposite side to the sensors' surface 358, namely facing away from the inner cavity 351. The LED light source 360 is illuminating a reflecting surface 364 such that the reflected light is detected by the photodiode detector 362 as exemplified by the arrow Light. A continuous detection of the reflected illumination of the photodiode detector 362 by a respective illumination of the LED light source 360 is being indicative to the movement of the substrate 354. For example, when force is applied on the substrate in the direction of arrow F than the substrate will deflect in the same direction and the photodiode detector 362 will detect a different intensity of reflected illumination by the LED light source 360 is the deflected state than in a steady state such as can best be seen in FIG. 13B. In this example, the sensor is worn on a wrist 366 by a wristband 368 and a portion of the skin 370 applies pressure on the substrate, causing it to move in the F direction. It should be noted that light intensity measured by the movement sensor can be interpreted to pressure and by that allow to instruct the user how tune the fastening strength to get the best performance per the chosen activity.

The movement sensor can be implemented in a device for sensing at least one biological parameter of an aspect of the present disclosure. When implemented, the at least one sensor of the sensing device are fixedly attached on an opposite side of the substrate such that at least a portion of the at least one sensor is on the same axis of at least one of the at least one light source and at least one detector of the movement sensor, the axis is defined to be perpendicular to the contact surface. In other words, the sensors, the light source and the detector disposed on opposite matching portions of the substrate. This configuration ensures that the movement sensor is substantially indicative to a force or pressure applied on the sensors.

Figure 14:
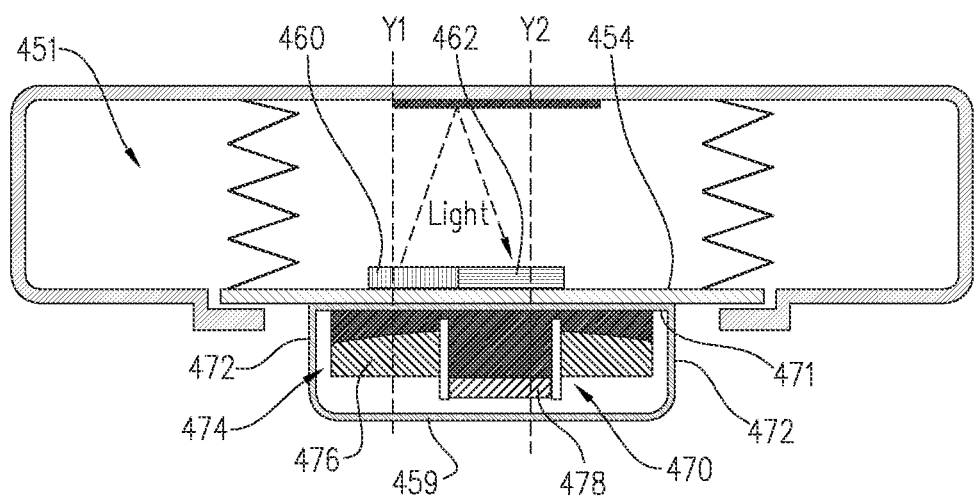
FIG. 14 is a schematic illustration of a longitudinal cross section of the sensing device of one aspect of the present disclosure comprising the movement sensor of another aspect of the present disclosure.

FIG. 14 is a schematic longitudinal cross section of an embodiment of the movement sensor implementation in the sensing device of an aspect of the present disclosure. The sensors 470, two light sources and a detector, are fixedly attached to the substrate 454, facing away from the cavity 451. The sensors 470 are accommodated within a void 474 formed between the substrate 454 and a barrier member 472, having a contact surface 459. The sensors 470 are fixedly attached to an outer face 471 of the substrate 454. The Barrier member 472 is rigidly integrated with the substrate 454 such that there is a full correlation between the movement of the barrier member 472 and the substrate 454. Therefore, a force applied on the contact surface 459 of the barrier member 472 is identified by respective illumination detected in the photodiode of the movement sensor. As can be appreciated, the sensing components from both sides of the substrate 454 share same longitudinal axes. For example, the sensing component 476 (e.g., a light source or an ECG sensor), is on the same longitudinal axis Y1 as the LED light source 460 and the sensing component 478 (e.g., a detector, or an ECG sensor) is on the same longitudinal axis Y2 as the photodiode detector 462. In this configuration, the measured movement of the contact surface 459, or calculated corresponding pressure applied thereon that caused the movement, have a relatively high accuracy. Other movement measurements devices, such as accelerometer, typically measure the movement in a position shifted from the measured biological parameter, has an inherent inaccuracy since they do not measure the exact position of the measurement. Even if the movement is relatively equal between the movement measurement and the biological parameter measurement, there is still a phase difference between the measurements that needs to take into consideration. The movement/pressure sensor of an aspect of the present disclosure provide a solution to overcome these problems.

Another aspect also provided by this disclosure is a sensing device for measuring at least one biological parameter, comprising a PPG sensor that comprises at least one light source and at least one detector for detecting at least a response of illumination of the at least one light source, said PPG sensor is laterally confined between two electrodes, typically ECG electrodes. At least a portion of the ECG electrodes is elevated with respect to the light source and the detector of the PPG sensor. The ECG electrodes are disposed in the device such that they do not obstruct the illumination cone of the light source and the detector of the PPG sensor, allowing a simultaneous measurement of ECG and PPG from a relatively small measured skin surface portion.

Figure 15:
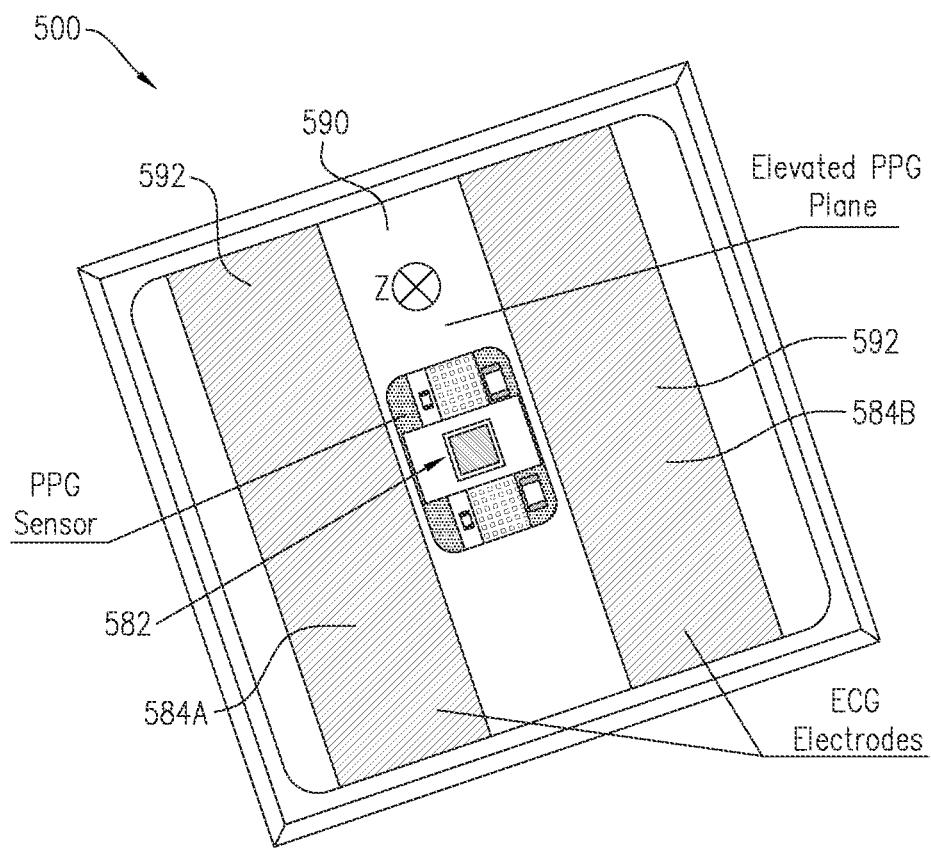
FIG. 15 is a top view of an embodiment of a sensing device of another aspect of the present disclosure.

FIG. 15 is a top view illustration of a sensing device 500 having a PPG sensor 582 confined between two ECG electrodes 584A, 584B. The PPG sensor has a light source 586 and a detector 588, both confined along a longitudinal axis Z such that the at least a portion of the ECG electrodes 584A, 584B is elevated with respect thereof in a direction facing away from the measurement device 500. As can be appreciated, the surfaces 590 and 592 span parallel planes along the axis Z.

The subject matter described above is provided by way of illustration only and should not be constructed as limiting. While certain features of the invention have been illustrated and described herein, many modifications, substitutions, changes, and equivalents will now occur to those skilled in the art.

The invention claimed is:

1. A device for sensing at least one biological parameter of a subject, the device comprising:
   a contact surface configured for being brought into a contact with a skin surface of the subject;
   at least one light source element for illuminating the skin surface through the contact surface along an illumination source optical axis with illumination including at least a first wavelength;
   at least one detector element that comprises a detector sensing surface, wherein the detector is configured for detecting a response of said illumination on the detector sensing surface from the skin surface through the contact surface along a detector optical axis, and providing signals indicative of said biological parameter based thereon;

wherein the light source element is disposed on said at least one detector element or disposed such that the geometric projection of the light source element on the plane defined by the detector element is entirely and continuously surrounded by said detector sensing surface of the detector element.

2. The device of claim 1, wherein the light source is a light emitting diode (LED) and the detector is a photodiode (PD).

3. The device of claim 1, wherein the light source is embedded within the detector.

4. The device of claim 1, comprising at least one different light source, surrounded in all lateral directions by the detector and configured for providing illumination comprising a second wavelength different from said first wavelength, and wherein said detector is configured for detecting a response of illumination from said different light source at said second wavelength, the first wavelength being within the green spectrum range and the second wavelength being within the violet spectrum, each of the first and second light sources disposed in a different distance from the detector.

5. The device of claim 1, further comprising a buffer surrounding the detector to obstruct light that is not reflected from the skin.

6. The device of claim 1, further comprising a housing coupled to a substrate by at least one flexible member, distinct from the housing and the substrate, to allow movement of the substrate and the contact surface with respect to the housing at least in the direction perpendicular to the contact surface, wherein the at least one light source and the at least one detector being disposed on the substrate;
the contact surface is rigidly integrated with the substrate such that there is a full correlation between the movement of the contact surface and the substrate.

7. The device of claim 6, comprising a movement and/or pressure sensor disposed on the substrate for sensing movement of and/or pressure applied on the contact surface.

8. A device for sensing at least one biological parameter of a subject, the device comprising:
a contact surface configured for being brought into a contact with a skin surface of the subject;
at least one light source element for illuminating the skin surface through the contact surface along an illumination source optical axis with illumination including at least a first wavelength;
at least one detector element that comprises a detector sensing surface, wherein the detector is configured for detecting a response of said illumination on the detector sensing surface from the skin surface through the contact surface along a detector optical axis, and providing signals indicative of said biological parameter based thereon;
wherein the light source element is disposed on said at least one detector element or disposed such that the geometric projection of the light source element on the plane defined by the detector element is entirely and continuously surrounded by and borders with the detector sensing surface of the detector.

9. A device for sensing at least one biological parameter of a subject, the device comprising:
a contact surface configured for being brought into a contact with a skin surface of the subject;
at least one light source element for illuminating the skin surface through the contact surface along an illumination source optical axis with illumination including at least a first wavelength;
at least one detector element configured for detecting a response of said illumination on from the skin surface through the contact surface along a detector optical axis, and providing signals indicative of said biological parameter based thereon;
wherein the light source element is disposed on said detector element or disposed such that the geometric projection of the light source element on the plane defined by the detector element is entirely and continuously surrounded by said detector element.

* * * * *